United States Patent [19]

Benatti et al.

[11] Patent Number: 6,136,572
[45] Date of Patent: Oct. 24, 2000

[54] RECOMBINANT KAT ENZYME AND PROCESS FOR ITS PREPARATION

[75] Inventors: Luca Benatti, Cologno Monzese; Jerome Breton, Milan; Carmela Speciale, Nerviano, all of Italy; Etsuo Okuno, Wakayama, Japan; Robert Schwarcz, Baltimore, Md.; Monica Mosca, Milan, Italy

[73] Assignees: University of Maryland at Baltimore, Baltimore, Md.; Pharmacia & Upjohn S.P.A., Milan, Italy

[21] Appl. No.: 08/765,889

[22] PCT Filed: Jun. 23, 1995

[86] PCT No.: PCT/US95/07855

§ 371 Date: Apr. 1, 1997

§ 102(e) Date: Apr. 1, 1997

[87] PCT Pub. No.: WO96/01893

PCT Pub. Date: Jan. 25, 1996

Related U.S. Application Data

[63] Continuation-in-part of application No. 08/271,667, Jul. 7, 1994, Pat. No. 5,817,496.

[51] Int. Cl.[7] .............................. C12P 17/00; C07H 21/04
[52] U.S. Cl. .......................... 435/117; 435/41; 435/193; 435/252.33; 435/325; 435/320.1; 536/23.2; 536/23.5
[58] Field of Search .............................. 435/193, 320.1, 435/252.3, 419, 325, 252.33; 536/23.2

[56] References Cited

FOREIGN PATENT DOCUMENTS 0 303 387  2/1989  European Pat. Off. .

OTHER PUBLICATIONS

Baran et al. *J. Neurochem.*, vol. 62, pp. 730–738, 1994.
Mawal et al. *J. Biochem.*, 279:595–599, 1991.
Takeuchi et al., *Biochem Biophys. Acta*, 743:323–330, 1983.
Suggs et al., *PNAS*, 78(11): 6613–6617, Nov. 1981.
Perry et al. "Molecular cloning and expression of a cDNA from human kidney . . . " FEBS Lett. 360, Mar. 6, 1995.
Perry et al., "Isolation and Expression of cDNA . . . " *Molecular Pharm..*, 43:660–665 (1993).
Baran et al., "Purification and Characterization . . . " *J. Neurochemistry*, 62:730–738 (1994).
Okuno et al., "Measurement of Rat Brain . . . " *J. Neurochemistry*, 57:533–540 (1991).
Alberati–Giani et al., "Cloning and Characterization . . . " *J. Neurochemistry* 64:1448–1455 (1995).
Mosca et al., "Molecular cloning of rat kynurenine . . . " *FEBS Letters*, 353:21–24 (1994).
Perry et al., "Molecular cloning and expression of a cDNA . . . " *FEBS Letters* 360:277–280, (1995).
Malherbe et al., "Identification of mitochondrial form of kynurenine . . . " *FEBS Letters* 367:141–144, (1995).

*Primary Examiner*—Nashaat Nashed
*Attorney, Agent, or Firm*—Sughrue, Mion, Zinn, Macpeak & Seas, PLLC

[57] ABSTRACT

Disclosed are isolated DNAs encoding a kynurenine aminotransferase selected from the group consisting of:

(a) isolated DNA sequences which encode rat KAT;

(b) an isolated DNA sequence which hybridizes to isolated DNA sequences of (a) above and which encodes a mammalian KAT enzyme; and (c) an isolated DNA sequence differing from the isolated DNA sequences of (a) and (b) above in codon sequence due to the degeneracy of the genetic code, and which encodes a KAT enzyme.

Vectors and host cells containing the same, oligonucleotide probes for identifying kynurenine aminotransferase, and isolated and purified kynurenine aminotransferase are also disclosed.

12 Claims, 17 Drawing Sheets

N - terminal

Leu-Gln-Ala-X-X-Leu-Asp-Gly-Ile-Asp-Gln-Asn-
Leu-X-Val-Glu-Phe-Gly-Lys-Thr-X-Glu-Tyr

CNBr fragment

X-X-Leu-Pro-Gly-Ala-Glu-Asp-Gly-Pro-Tyr-Asp-Arg
-Arg-X-Ala

Tryptic fragment 112

Arg-Leu-Asp-Gly-Ile-Asp-Gln-Asn-Leu-Ser-Val-
Glu-Phe-Gly

Tryptic fragment 130

X-Glu-Leu-Glu-Leu-Val-Ala-Asn-Leu-Cys-Gln-Gln-His
Asp-Val-Cys-Ile-Ser-Asp-Glu-Val-Tyr-Gln-Gln-Val-Tyr-
Asp-Leu-Gly-His-Gln

FIG. 1

```
          10        20        30        40        50        60
 1234567890123456789012345678901234567890123456789012345678901234567890
AAACTGACCAAGGAGTATGATCAATCCCGTCCAGCCTCCGAGCCTGCAGCCGTTTGGTCA          60

TGGTGAGCTGCTTCAGCTAACAATTGCACTGACAGTGCTCTTGAGCCAAGTTGCTTCTGG         120

GCGGAAGTAGTCCATCTAGGGCTCGGCCTCTTTAAAGAAACAGACTTCTGCAACCTTGGG         180

ACTACGTTTGGGGTCGCCGGCTATTGGACGGAGCAGCGCAATTGTTAGCTGAAGCAGCTC         240

ACCATGACCAAACGGCTGCAGGCTCGGAGGCTGGACGGGATTGATCAAAACCTCTGGGTG         300
   MetThrLysArgLeuGlnAlaArgArgLeuAspGlyIleAspGlnAsnLeuTrpVal
```

```
GAGTTTGGCAAACTGACCAAGGAGTATGACGTCGTGAACTTGGGTCAGGGCTTCCCTGAC         360
GluPheGlyLysLeuThrLysGluTyrAspValValAsnLeuGlyGlnGlyPheProAsp

TTCTCGCCTCCGGACTTTGCAACGCAAGCTTTTCAGCAGGCTACCAGTGGGAACTTCATG         420
PheSerProProAspPheAlaThrGlnAlaPheGlnGlnAlaThrSerGlyAsnPheMet

CTCAACCAGTACACCAGGGCATTTGGTTACCCACCACTGACAAACGTCCTGGCAAGTTTC         480
LeuAsnGlnTyrThrArgAlaPheGlyTyrProProLeuThrAsnValLeuAlaSerPhe

TTTGGCAAGCTGCTGGGACAGGAGATGGACCCACTCACGAATGTGCTGGTGACAGTGGGT         540
PheGlyLysLeuLeuGlyGlnGluMetAspProLeuThrAsnValLeuValThrValGly

GCCTATGGGGCCTTGTTCACAGCTTTCAGGCCCTGGTGGATGAAGGAGATGAGGTCATC         600
AlaTyrGlyAlaLeuPheThrAlaPheGlnAlaLeuValAspGluGlyAspGluValIle

ATCATGGAACCTGCTTTTGACTGTTATGAACCCATGACAATGATGGCTGGAGGTTGCCCT         660
IleMetGluProAlaPheAspCysTyrGluProMetThrMetMetAlaGlyGlyCysPro

GTGTTCGTGACTCTGAAGCCGAGCCCTGCTCCTAAGGGGAAACTGGGAGCCAGCAATGAT         720
ValPheValThrLeuLysProSerProAlaProLysGlyLysLeuGlyAlaSerAsnAsp

TGGCAACTGGATCCTGCAGAACTGGCCAGCAAGTTCACACCTCGCACCAAGGTCCTGGTC         780
TrpGlnLeuAspProAlaGluLeuAlaSerLysPheThrProArgThrLysValLeuVal

CTCAACACACCCAACAACCCTTTAGGAAAGGTATTCTCTAGGATGGAGCTGGAGCTGGTG         840
LeuAsnThrProAsnAsnProLeuGlyLysValPheSerArgMetGluLeuGluLeuVal

GCTAATCTGTGCCAGCAGCACGATGTCGTGTGCATCTCTGATGAGGTCTACCAGTGGCTG         900
AlaAsnLeuCysGlnGlnHisAspValValCysIleSerAspGluValTyrGlnTrpLeu
```

FIG. 2A

```
            10        20        30        40        50        60
   1234567890123456789012345678901234567890123456789012345678901234567890
   GTCTATGACGGGCACCAGCACGTCAGCATCGCCAGCCTCCCTGGCATGTGGGATCGGACC           960
   ValTyrAspGlyHisGlnHisValSerIleAlaSerLeuProGlyMetTrpAspArgThr

CTGACCATCGGCAGTGCAGGCAAAAGCTTCAGTGCCACTGGCTGGAAGGTGGGCTGGGTC          1020
   LeuThrIleGlySerAlaGlyLysSerPheSerAlaThrGlyTrpLysValGlyTrpVal

ATGGGTCCAGATAACATCATGAAGCACCTGAGGACAGTGCACCAGAATTCTATCTTCCAC          1080
   MetGlyProAspAsnIleMetLysHisLeuArgThrValHisGlnAsnSerIlePheHis

TGCCCCACCCAGGCCCAGGCTGCAGTAGCCCAGTGCTTTGAGCGGGAGCAGCAACACTTT          1140
   CysProThrGlnAlaGlnAlaAlaValAlaGlnCysPheGluArgGluGlnGlnHisPhe

GGACAACCCAGCAGCTACTTTTTGCAGCTGCCACAGGCCATGGAGCTGAACCGAGACCAC          1200
   GlyGlnProSerSerTyrPheLeuGlnLeuProGlnAlaMetGluLeuAsnArgAspHis

ATGATCCGTAGCCTGCAGTCAGTGGGCCTCAAGCTCTGGATCTCCAGGGGAGCTACTTC          1260
   MetIleArgSerLeuGlnSerValGlyLeuLysLeuTrpIleSerGlnGlySerTyrPhe

CTCATTGCAGACATCTCAGACTTCAAGAGCAAGATGCCTGACCTGCCCGGAGCTGAGGAT          1320
   LeuIleAlaAspIleSerAspPheLysSerLysMetProAspLeuProGlyAlaGluAsp

GAGCCTTATGACAGACGCTTTGCCAAGTGGATGATCAAAAACATGGGCTTGGTGGGCATC         1380
   GluProTyrAspArgArgPheAlaLysTrpMetIleLysAsnMetGlyLeuValGlyIle

CCTGTCTCCACATTCTTCAGTCGGCCCCATCAGAAGGACTTTGACCACTACATCCGATTC         1440
   ProValSerThrPhePheSerArgProHisGlnLysAspPheAspHisTyrIleArgPhe

TGTTTTGTCAAGGACAAGGCCACACTCCAGGCCATGGATGAGAGACTGCGCAAGTGGAAA         1500
   CysPheValLysAspLysAlaThrLeuGlnAlaMetAspGluArgLeuArgLysTrpLys

GAGCTCCAACCCTGAGGAGGCTGCCCTCAGCCCCACCTCGAACACAGGCCTCAGCTATGC         1560
   GluLeuGlnPro

CTTAGCACAGGGATGGCACTGGAGGGCCCAGCTGTGTGACTGCGCATGTTTCCAGAAAAG         1620

AGGCCATGTCTTGGGGGTTGAAGCCATCCTTTCCCAGTGTCCATCTGGACTATTGGGTTG         1680

GGGGCCAGTTCTGGGTCTCAGCCTACTCCTCTGTAGGTTGCCTGTAGGGTTTTGATTGTT         1740

TCTGGCCTCTCTGCCTGGGGCAGGAAAGGGTGGAATATCAGGCCCGGTACCACCTTAGCC         1800
```

FIG. 2B

```
        10        20        30        40        50        60
1234567890123456789012345678901234567890123456789012345678901234567890
CTGCCGAGGCTCTGTGGCTTCTCTACATCTTCTCCTGTGACCTCAGGATGTTGCTACTGT              1860

TCCTAATAAAGTTTTAAGTTATTAGGACCCTCA                                         1893
```

FIG. 2C

```
         10        20        30        40        50        60
123456789012345678901234567890123456789012345678901234567890
GGGCGACTCTAGATTTTTTTTTTTTTTACCTTCTACCTTTTATTGTCACGTGAACCATG    60

GTCCTACAGGCTGCTGACAAGCTTGGCTGAGCAGGGATCCAGGGGCGTCGGCAGGAGAT   120

GAGGAAGGGTTGCTGGGAGGGCTTGGCCTCTTCCTTGAGAAGACAGCAAATGTATCCAGC  180

CTAGATTAAGGGTAGGGCATCCCTATCCCTGTCAGTGGGCTAGATCTCAGAGCCCCAC    240

ATTAAAGACTGCTAATGGGTCAGAAATGGGGTCCCTTAGATGGGGTAGGCAGCAAGGC    300

CCTCCCTCCAGTGTTCTCATTCTGTTCCGGTTTCATTTGTTGTGTCCAGGGACGGTGAAG  360

CAGATACCAGTCTCAAGCCCCAGGGTGCAGGAAGACGGGAAATGGGAAAATGGAAACATT  420

CTTCAAGTGACCAGAGCACTCTGCCGGGGACAAAAGACTTTGCCTTGAACGCGTAGTGGA  480

GAAGCTACAAACCCCAGGTCCCAGTGGCCTGATTGACTTAGGGTCTCAGCTGGCCCAAAA  540

CTCAGTGTGTAGATCAGACTGATCTCAAACTCACAGAGATCTCCCTGCCTTTGCCTGCTG  600

AGTCCTGGGATTAAAGGCATGAATCACAGTACCTGGTGCCTTTTCTTTAAAAAGCTCACC  660
             MetAsnHisSerThrTrpCysLeuPhePheLysLysLeuThr
```

FIG. 3A

```
          10        20        30        40        50        60
 1234567890123456789012345678901234567890123456789012345678901234567890
 ATGACCAAACGGCTGCAGGCTCGGAGGCTGGACGGGATTGATCAAAACCTCTGGGTGGAG            720
 MetThrLysArgLeuGlnAlaArgArgLeuAspGlyIleAspGlnAsnLeuTrpValGlu
 MetThrLysArgLeuGlnAlaArgArgLeuAspGlyIleAspGlnAsnLeuTrpValGlu

TTTGGCAAACTGACCAAGGAGTATGACGTCGTGAACTTGGGTCAGGGCTTTCCCTGACTTC           780
 PheGlyLysLeuThrLysGluTyrAspValValAsnLeuGlyGlnGlyPheProAspPhe
 PheGlyLysLeuThrLysGluTyrAspValValAsnLeuGlyGlnGlyPheProAspPhe

TCGCCTCCGGACTTTGCAACGCAAGCTTTTCAGCAGGCTACCAGTGGGAACTTCATGCTC           840
 SerProProAspPheAlaThrGlnAlaPheGlnGlnAlaThrSerGlyAsnPheMetLeu
 SerProProAspPheAlaThrGlnAlaPheGlnGlnAlaThrSerGlyAsnPheMetLeu

AACCAGTACACCAGGGCATTTGGTTACCCACCACTGACAAACGTCCTGGCAAGTTTCTTT           900
 AsnGlnTyrThrArgAlaPheGlyTyrProProLeuThrAsnValLeuAlaSerPhePhe
 AsnGlnTyrThrArgAlaPheGlyTyrProProLeuThrAsnValLeuAlaSerPhePhe

GGCAAGCTGCTGGGACAGGAGATGGACCCACTCACGAATGTGCTGGTGACAGTGGGTGCC          960
 GlyLysLeuLeuGlyGlnGluMetAspProLeuThrAsnValLeuValThrValGlyAla
 GlyLysLeuLeuGlyGlnGluMetAspProLeuThrAsnValLeuValThrValGlyAla

TATGGGGCCTTGTTCACAGCGTTTCAGGCCCTGGTGGATGAAGGAGATGAGGTCATCATC        1020
 TyrGlyAlaLeuPheThrAlaPheGlnAlaLeuValAspGluGlyAspGluValIleIle
 TyrGlyAlaLeuPheThrAlaPheGlnAlaLeuValAspGluGlyAspGluValIleIle

ATGGAACCTGCTTTTGACTGTTATGAACCCATGACAATGATGGCTGGAGGTTGCCCTGTG        1080
 MetGluProAlaPheAspCysTyrGluProMetThrMetMetAlaGlyGlyCysProVal
 MetGluProAlaPheAspCysTyrGluProMetThrMetMetAlaGlyGlyCysProVal

TTCGTGACTCTGAAGCCGAGCCCTGCTCCTAAGGGGAAACTGGGAGCCAGCAATGATTGG        1140
 PheValThrLeuLysProSerProAlaProLysGlyLysLeuGlyAlaSerAsnAspTrp
 PheValThrLeuLysProSerProAlaProLysGlyLysLeuGlyAlaSerAsnAspTrp

CAACTGGATCCTGCAGAACTGGCCAGCAAGTTCACACCTCGCACCAAGGTGCTGGTCCTC       1200
 GlnLeuAspProAlaGluLeuAlaSerLysPheThrProArgThrLysValLeuValLeu
 GlnLeuAspProAlaGluLeuAlaSerLysPheThrProArgThrLysValLeuValLeu

AACACACCCAACAACCCTTTAGGAAAGGTATTCTCTAGGATGGAGCTGGAGCTGGTGGCT      1260
 AsnThrProAsnAsnProLeuGlyLysValPheSerArgMetGluLeuGluLeuValAla
 AsnThrProAsnAsnProLeuGlyLysValPheSerArgMetGluLeuGluLeuValAla

AATCTGTGCCAGCAGCACGATGTCGTGTGCATCTCTGATGAGGTCTACCAGTGGCTGGTC     1320
 AsnLeuCysGlnGlnHisAspValValCysIleSerAspGluValTyrGlnTrpLeuVal
 AsnLeuCysGlnGlnHisAspValValCysIleSerAspGluValTyrGlnTrpLeuVal
```

FIG. 3B

```
              10        20        30        40        50        60
     1234567890123456789012345678901234567890123456789012345678901234567890
     TATGACGGGCACCAGCACGTCAGCATCGCCAGCCTCCCTGGCATGTGGGATCGGACCCTG              1380
     TyrAspGlyHisGlnHisValSerIleAlaSerLeuProGlyMetTrpAspArgThrLeu
     TyrAspGlyHisGlnHisValSerIleAlaSerLeuProGlyMetTrpAspArgThrLeu

ACCATCGGCAGTGCAGGCAAAAGCTTCAGTGCCACTGGCTGGAAGGTGGGCTGGGTCATG              1440
     ThrIleGlySerAlaGlyLysSerPheSerAlaThrGlyTrpLysValGlyTrpValMet
     ThrIleGlySerAlaGlyLysSerPheSerAlaThrGlyTrpLysValGlyTrpValMet

GGTCCAGATAACATCATGAAGCACCTGAGGACAGTGCACCAGAATTCTATCTTCCACTGC              1500
     GlyProAspAsnIleMetLysHisLeuArgThrValHisGlnAsnSerIlePheHisCys
     GlyProAspAsnIleMetLysHisLeuArgThrValHisGlnAsnSerIlePheHisCys

CCCACCCAGGCCCAGGCTGCAGTAGCCCAGTGCTTTGAGCGGGAGCAGCAACACTTTGGA              1560
     ProThrGlnAlaGlnAlaAlaValAlaGlnCysPheGluArgGluGlnGlnHisPheGly
     ProThrGlnAlaGlnAlaAlaValAlaGlnCysPheGluArgGluGlnGlnHisPheGly

CAACCCAGCAGCTACTTTTTGCAGCTGCCACAGGCCATGGAGCTGAACCGAGACCACATG              1620
     GlnProSerSerTyrPheLeuGlnLeuProGlnAlaMetGluLeuAsnArgAspHisMet
     GlnProSerSerTyrPheLeuGlnLeuProGlnAlaMetGluLeuAsnArgAspHisMet

ATCCGTAGCCTGCAGTCAGTGGGCCTCAAGCTCTGGATCTCCCAGGGGAGCTACTTCCTC              1680
     IleArgSerLeuGlnSerValGlyLeuLysLeuTrpIleSerGlnGlySerTyrPheLeu
     IleArgSerLeuGlnSerValGlyLeuLysLeuTrpIleSerGlnGlySerTyrPheLeu

ATTGCAGACATCTCAGACTTCAAGAGCAAGATGCCTGACCTGCCCGGAGCTGAGGATGAG              1740
     IleAlaAspIleSerAspPheLysSerLysMetProAspLeuProGlyAlaGluAspGlu
     IleAlaAspIleSerAspPheLysSerLysMetProAspLeuProGlyAlaGluAspGlu

CCTTATGACAGACGCTTTGCCAAGTGGATGATCAAAAACATGGGCTTGGTGGGCATCCCT              1800
     ProTyrAspArgArgPheAlaLysTrpMetIleLysAsnMetGlyLeuValGlyIlePro
     ProTyrAspArgArgPheAlaLysTrpMetIleLysAsnMetGlyLeuValGlyIlePro

GTCTCCACATTCTTCAGTCGGCCCCATCAGAAGGACTTTGACCACTACATCCGATTCTGT              1860
     ValSerThrPhePheSerArgProHisGlnLysAspPheAspHisTyrIleArgPheCys
     ValSerThrPhePheSerArgProHisGlnLysAspPheAspHisTyrIleArgPheCys

TTTGTCAAGGACAAGGCCACACTCCAGGCCATGGATGAGAGACTGCGCAAGTGGAAAGAG              1920
     PheValLysAspLysAlaThrLeuGlnAlaMetAspGluArgLeuArgLysTrpLysGlu
     PheValLysAspLysAlaThrLeuGlnAlaMetAspGluArgLeuArgLysTrpLysGlu

CTCCAACCCTGAGGAGGCTGCCCTCAGCCCCACCTCGAACACAGGCCTCAGCTATGCCTT              1980
     LeuGlnPro
     LeuGlnPro
```

FIG. 3C

```
          10        20        30        40        50        60
 123456789012345678901234567890123456789012345678901234567890
 AGCACAGGGATGGCACTGGAGGGCCAGCTGTGTGACTGCGCATGTTTCCAGAAAAGAGG    2040

CCATGTCTTGGGGGTTGAAGCCATCCTTTCCCAGTGTCCATCTGGACTATTGGGTTGGGG   2100

GCCAGTTCTGGGTCTCAGCCTACTCCTCTGTAGGTTGCCTGTAGGGTTTTGATTGTTTCT   2160

GGCCTCTCTGCCTGGGGCAGGAAAGGGTGGAATATCAGGCCCGGTACCACCTTAGCCCTG   2220

CCGAGGCTCTGTGGCTTCTCTACATCTTCTCCTGTGACCTCAGGATGTTGCTACTGTTCC   2280

TAATAAAGTTTTAAGTTATTAGGA                                       2304
```

FIG. 3D

```
                10        20        30        40        50        60
       1234567890123456789012345678901234567890123456789012345678901234567890
       AAACTGACCAAGGAGTATGATCAATCCCGTCCAGCCTCCGAGCCTGCAGCCGTTTGGTCA              60

TGGTGAGCTGCTTCAGCTAACAATTGCACTGACAGTGCTCTTGAGCCAAGTTGCTTCTGG            120

GCGGAAGTAGTCCATCTAGGGCTCGGCCTCTTTAAAGAAACAGACTTCTGCAACCTTGGG            180

ACTACGTTTGGGGTCGCCGGCTATTGGACGGAGCAGCGCAATTGTTAGCTGAAGCAGAAC            240

TGTGTGTGGACTCAGGCCCTGGCTTGGAGCCATTTTCTGGGCTAGGCTGTCTGCCCTTCT            300

GTCCCTCTGGAGGGAAGCCTGCAGTGCCTGTGGACCTACCTCAGAGGCATGTTCAGGAG             360
                                                         MetPheArgSe

TGCAGCAGCCCTCTCGGTGCACCTGATGTGGCCACTCTGGGAAGGAAAGCTGGAGCCTC             420
       rAlaAlaAlaLeuSerValHisLeuMetTrpProLeuTrpGlyArgLysAlaGlyAlaSe

ACTCACCCGGTGCTTGCACCAGTCTCTCACCATGACCAAACGGCTGCAGGCTCGGAGGCT            480
       rLeuThrArgCysLeuHisGlnSerLeuThrMetThrLysArgLeuGlnAlaArgArgLe
                                   MetThrLysArgLeuGlnAlaArgArgLe

GGACGGGATTGATCAAAACCTCTGGGTGGAGTTTGGCAAACTGACCAAGGAGTATGACGT            540
       uAspGlyIleAspGlnAsnLeuTrpValGluPheGlyLysLeuThrLysGluTyrAspVa
       uAspGlyIleAspGlnAsnLeuTrpValGluPheGlyLysLeuThrLysGluTyrAspVa

TGTGAACTTGGGTCAGGGCTTCCCTGACTTCTCGCCTCCGGACTTTGCAACGCAAGCTTT            600
       lValAsnLeuGlyGlnGlyPheProAspPheSerProProAspPheAlaThrGlnAlaPh
       lValAsnLeuGlyGlnGlyPheProAspPheSerProProAspPheAlaThrGlnAlaPh

TCAGCAGGCTACCAGTGGGAACTTCATGCTCAACCAGTACACCAGGGCATTTGGTTACCC            660
       eGlnGlnAlaThrSerGlyAsnPheMetLeuAsnGlnTyrThrArgAlaPheGlyTyrPr
       eGlnGlnAlaThrSerGlyAsnPheMetLeuAsnGlnTyrThrArgAlaPheGlyTyrPr
```

FIG. 4A

```
              10        20        30        40        50        60
     1234567890123456789012345678901234567890123456789012345678901234567890
     ACCACTGACAAACGTCCTGGCAAGTTTCTTTGGCAAGCTGCTGGGACAGGAGATGGACCC    720
    oProLeuThrAsnValLeuAlaSerPhePheGlyLysLeuLeuGlyGlnGluMetAspPr
    oProLeuThrAsnValLeuAlaSerPhePheGlyLysLeuLeuGlyGlnGluMetAspPr

ACTCACGAATGTGCTGGTGACAGTGGGTGCCTATGGGGCCTTGTTCACAGCCTTTCAGGC    780
    oLeuThrAsnValLeuValThrValGlyAlaTyrGlyAlaLeuPheThrAlaPheGlnAl
    oLeuThrAsnValLeuValThrValGlyAlaTyrGlyAlaLeuPheThrAlaPheGlnAl

CCTGGTGGATGAAGGAGATGAGGTCATCATCATGGAACCTGCTTTTGACTGTTATGAACC    840
    aLeuValAspGluGlyAspGluValIleIleMetGluProAlaPheAspCysTyrGluPr
    aLeuValAspGluGlyAspGluValIleIleMetGluProAlaPheAspCysTyrGluPr

CATGACAATGATGGCTGGAGGTTGCCCTGTGTTCGTGACTCTGAAGCCGAGCCCTGCTCC    900
    oMetThrMetMetAlaGlyGlyCysProValPheValThrLeuLysProSerProAlaPr
    oMetThrMetMetAlaGlyGlyCysProValPheValThrLeuLysProSerProAlaPr

TAAGGGAAACTGGGAGCCAGCAATGATTGGCAACTGGATCCTGCAGAACTGGCCAGCAA     960
    oLysGlyLysLeuGlyAlaSerAsnAspTrpGlnLeuAspProAlaGluLeuAlaSerLy
    oLysGlyLysLeuGlyAlaSerAsnAspTrpGlnLeuAspProAlaGluLeuAlaSerLy

GTTCACACCTCGCACCAAGGTCCTGGTCCTCAACACACCCAACAACCCTTTAGGAAAGGT    1020
    sPheThrProArgThrLysValLeuValLeuAsnThrProAsnAsnProLeuGlyLysVa
    sPheThrProArgThrLysValLeuValLeuAsnThrProAsnAsnProLeuGlyLysVa

ATTCTCTAGGATGGAGCTGGAGCTGGTGGCTAATCTGTGCCAGCAGCACGATGTCGTGTG    1080
    lPheSerArgMetGluLeuGluLeuValAlaAsnLeuCysGlnGlnHisAspValValCy
    lPheSerArgMetGluLeuGluLeuValAlaAsnLeuCysGlnGlnHisAspValValCy

CATCTCTGATGAGGTCTACCAGTGGCTGGTCTATGACGGGCACCAGCACGTCAGCATCGC    1140
    sIleSerAspGluValTyrGlnTrpLeuValTyrAspGlyHisGlnHisValSerIleAl
    sIleSerAspGluValTyrGlnTrpLeuValTyrAspGlyHisGlnHisValSerIleAl

CAGCCTCCCTGGCATGTGGGATCGGACCCTGACCATCGGCAGTGCAGGCAAAAGCTTCAG    1200
    aSerLeuProGlyMetTrpAspArgThrLeuThrIleGlySerAlaGlyLysSerPheSe
    aSerLeuProGlyMetTrpAspArgThrLeuThrIleGlySerAlaGlyLysSerPheSe

TGCCACTGGCTGGAAGGTGGGCTGGGTCATGGGTCCAGATAACATCATGAAGCACCTGAG    1260
    rAlaThrGlyTrpLysValGlyTrpValMetGlyProAspAsnIleMetLysHisLeuAr
    rAlaThrGlyTrpLysValGlyTrpValMetGlyProAspAsnIleMetLysHisLeuAr

GACAGTGCACCAGAATTCTATCTTCCACTGCCCCACCCAGGCCCAGGCTGCAGTAGCCCA    1320
    gThrValHisGlnAsnSerIlePheHisCysProThrGlnAlaGlnAlaAlaValAlaGl
    gThrValHisGlnAsnSerIlePheHisCysProThrGlnAlaGlnAlaAlaValAlaGl
```

FIG. 4B

```
          10        20        30        40        50        60
 1234567890123456789012345678901234567890123456789012345678901234567890
GTGCTTTGAGCGGGAGCAGCAACACTTTGGACAACCCAGCAGCTACTTTTTGCAGCTGCC      1380
 nCysPheGluArgGluGlnGlnHisPheGlyGlnProSerSerTyrPheLeuGlnLeuPr
 nCysPheGluArgGluGlnGlnHisPheGlyGlnProSerSerTyrPheLeuGlnLeuPr

ACAGGCCATGGAGCTGAACCGAGACCACATGATCCGTAGCCTGCAGTCAGTGGGCCTCAA      1440
 oGlnAlaMetGluLeuAsnArgAspHisMetIleArgSerLeuGlnSerValGlyLeuLy
 oGlnAlaMetGluLeuAsnArgAspHisMetIleArgSerLeuGlnSerValGlyLeuLy

GCTCTGGATCTCCCAGGGGAGCTACTTCCTCATTGCAGACATCTCAGACTTCAAGAGCAA      1500
 sLeuTrpIleSerGlnGlySerTyrPheLeuIleAlaAspIleSerAspPheLysSerLy
 sLeuTrpIleSerGlnGlySerTyrPheLeuIleAlaAspIleSerAspPheLysSerLy

GATGCCTGACCTGCCCGGAGCTGAGGATGAGCCTTATGACAGACGCTTTGCCAAGTGGAT      1560
 sMetProAspLeuProGlyAlaGluAspGluProTyrAspArgArgPheAlaLysTrpMe
 sMetProAspLeuProGlyAlaGluAspGluProTyrAspArgArgPheAlaLysTrpMe

GATCAAAAACATGGGCTTGGTGGGCATCCCTGTCTCCACATTCTTCAGTCGGCCCCATCA      1620
 tIleLysAsnMetGlyLeuValGlyIleProValSerThrPhePheSerArgProHisGl
 tIleLysAsnMetGlyLeuValGlyIleProValSerThrPhePheSerArgProHisGl

GAAGGACTTTGACCACTACATCCGATTCTGTTTTGTCAAGGACAAGGCCACACTCCAGGC      1680
 nLysAspPheAspHisTyrIleArgPheCysPheValLysAspLysAlaThrLeuGlnAl
 nLysAspPheAspHisTyrIleArgPheCysPheValLysAspLysAlaThrLeuGlnAl

CATGGATGAGAGACTGCGCAAGTGGAAAGAGCTCCAACCCTGAGGAGGCTGCCCTCAGCC      1740
 aMetAspGluArgLeuArgLysTrpLysGluLeuGlnPro
 aMetAspGluArgLeuArgLysTrpLysGluLeuGlnPro

CCACCTCGAACACAGGCCTCAGCTATGCCTTAGCACAGGGATGGCACTGGAGGGCCCAGC      1800

TGTGTGACTGCGCATGTTTCCAGAAAAGAGGCCATCTCTTGGGGGTTGAAGCCATCCTTT      1860

CCCAGTGTCCATCTGGACTATTGGGTTGGGGGCCAGTTCTGGGTCTCAGCCTACTCCTCT      1920

GTAGGTTGCCTGTAGGGTTTTGATTGTTTCTGGCCTCTCTGCCTGGGCAGGAAAGGGTG      1980

FIG. 4C
```

```
          10        20        30        40        50        60
 1234567890123456789012345678901234567890123456789012345678901234567890
 GAATATCAGGCCCGGTACCACCTTAGCCCTGCCGAGGCTCTGTGGCTTCTCTACATCTTC    2040

TCCTGTGACCTCAGGATGTTGCTACTGTTCCTAATAAAGTTTTAAGTTATTAGGACCCTC    2100

Tryptic fragment F11

Thr-Phe-Ser-Ala-Thr-Gly-XXX-Lys

The sequence corresponds to positions 191-198 of the protein deduced from the human brain cDNA sequence Tryptic fragment F13

Ala-Leu-Val-Leu-Asn-Thr-Pro-Asn-Asn-Pro-Leu-Gly-Lys

The sequence corresponds to positions 120-132 of the protein deduced from the human brain cDNA sequence Tryptic fragment F14

Glu-Gln-Leu-Leu-Phe-Arg

The sequence corresponds to positions 238-243 of the protein deduced from the human brain cDNA sequence

FIG. 6

```
         10        20        30        40        50        60
1234567890123456789012345678901234567890123456789012345678901234567890
CTTAATGTTTTTAGAGCTCACCATGGCCAAACAGCTGCAGGCCCGAAGGCTAGACGGGAT         60
                  MetAlaLysGlnLeuGlnAlaArgArgLeuAspGlyIl

CGACTACAACCCCTGGGTGGAGTTTGTGAAACTGGCCAGTGAGCATGACGTCGTGAACTT         120
eAspTyrAsnProTrpValGluPheValLysLeuAlaSerGluHisAspValValAsnLe

GGGCCAGGGCTTCCCGGATTTCCCACCACCAGACTTTGCCGTGGAAGCCTTTCAGCACGC         180
uGlyGlnGlyPheProAspPheProProProAspPheAlaValGluAlaPheGlnHisAl

TGTCAGTGGAGACTTCATGCTTAACCAGTACACCAAGACATTTGGTTACCCACCACTGAC         240
aValSerGlyAspPheMetLeuAsnGlnTyrThrLysThrPheGlyTyrProProLeuTh

GAAGATCCTGGCAAGTTTCTTTGGGGAGCTGCTGGGTCAGGAGATAGACCCGCTCAGGAA         300
rLysIleLeuAlaSerPhePheGlyGluLeuLeuGlyGlnGluIleAspProLeuArgAs

TGTGCTGGTGACTGTTGGTGGCTATGGGGCCCTGTTCACAGCCTTCCAGGCCCTGGTGGA         360
nValLeuValThrValGlyGlyTyrGlyAlaLeuPheThrAlaPheGlnAlaLeuValAs

CGAAGGAGACGAGGTCATCATCATCGAACCCTTTTTTGACTGCTACGAGCCCATGACAAT         420
pGluGlyAspGluValIleIleIleGluProPhePheAspCysTyrGluProMetThrMe

GATGGCAGGGGGTCGTCCTGTGTTTGTGTCCCTGAAGCCGGGTCCCATCCAGAATGGAGA         480
tMetAlaGlyGlyArgProValPheValSerLeuLysProGlyProIleGlnAsnGlyGl

ACTGGGTTCCAGCAGCAACTGGCAGCTGGACCCCATGGAGCTGGCCGGCAAATTCACATC         540
uLeuGlySerSerSerAsnTrpGlnLeuAspProMetGluLeuAlaGlyLysPheThrSe

ACGCACCAAAGCCCTGGTCCTCAACACCCCCAACAACCCCCTGGGCAAGGTGTTCTCCAG         600
rArgThrLysAlaLeuValLeuAsnThrProAsnAsnProLeuGlyLysValPheSerAr

GGAAGAGCTGGAGCTGGTGGCCAGCCTTTGCCAGCAGCATGACGTGGTGTGTATCACTGA         660
gGluGluLeuGluLeuValAlaSerLeuCysGlnGlnHisAspValValCysIleThrAs
```

FIG. 7A

```
          10        20        30        40        50        60
 1234567890123456789012345678901234567890123456789012345678901234567890
TGAAGTCTACCAGTGGATGGTCTACGACGGGCACCAGCACATCAGCATTGCCAGCCTCCC         720
pGluValTyrGlnTrpMetValTyrAspGlyHisGlnHisIleSerIleAlaSerLeuPr

TGGCATGTGGGAACGGACCCTGACCATCGGCAGCGCCGGCAAGACCTTCAGCGCCACTGG         780
oGlyMetTrpGluArgThrLeuThrIleGlySerAlaGlyLysThrPheSerAlaThrGl

CTGGAAGGTGGGCTGGGTCCTGGGTCCAGATCACATCATGAAGCACCTGCGGACCGTGCA         840
yTrpLysValGlyTrpValLeuGlyProAspHisIleMetLysHisLeuArgThrValHi

CCAGAACTCCGTCTTCCACTGCCCCACGCAGAGCCAGGCTGCAGTAGCCGAGAGCTTTGA         900
sGlnAsnSerValPheHisCysProThrGlnSerGlnAlaAlaValAlaGluSerPheGl

ACGGGAGCAGCTGCTCTTCCGCCAACCCAGCAGCTACTTTGTGCAGTTCCCGCAGGCCAT         960
uArgGluGlnLeuLeuPheArgGlnProSerSerTyrPheValGlnPheProGlnAlaMe

GCAGCGCTGCCGTGACCACATGATACGTAGCCTACAGTCAGTGGGCCTGAAGCCCATCAT        1020
tGlnArgCysArgAspHisMetIleArgSerLeuGlnSerValGlyLeuLysProIleIl

CCCTCAGGGCAGCTACTTCCTCATCACAGACATCTCAGACTTCAAGAGGAAGATGCCTGA        1080
eProGlnGlySerTyrPheLeuIleThrAspIleSerAspPheLysArgLysMetProAs

CTTGCCTGGAGCTGTGGATGAGCCCTATGACAGACGCTTCGTCAAGTGGATGATCAAGAA        1140
pLeuProGlyAlaValAspGluProTyrAspArgArgPheValLysTrpMetIleLysAs

CAAGGGCTTGGTGGCCATCCCTGTCTCCATCTTCTATAGTGTGCCACATCAGAAGCACTT        1200
nLysGlyLeuValAlaIleProValSerIlePheTyrSerValProHisGlnLysHisPh

TGACCACTATATCCGCTTCTGTTTTGTGAAGGATGAAGCCACGCTCCAGGCCATGGACGA        1260
eAspHisTyrIleArgPheCysPheValLysAspGluAlaThrLeuGlnAlaMetAspGl

GAAGCTGCGGAAGTGGAAGGTGGAACTCTAGCCCTGAAGTCACGCCTTGGCCCTGACATC        1320
uLysLeuArgLysTrpLysValGluLeu...
```

FIG. 7B

```
          10        20        30        40        50        60
 123456789012345678901234567890123456789012345678901234567890
 CCCACATGCCCGCAGAGATCCTCTTTGAGTGTCTGTCTTTGTCCAGGTTTCAGACATTTC   1380

TAGGTTGGGGAAGATGCTATTGGGAAACCTCTTCTCCGTGACACAGAATGTTCTGGGTGG   1440

GAGCCGCCCTTCTTCATCTTAGAGAACCAAGTACCTCCTGTCTGAAAGGTGAGGGTGGCC   1500

TGACCTGGGCCTCTCCCTGCCCCTCCATAGGTGGGTTTGTAGGGTCTTGTGTTGCTTCTG   1560

GTCTCTCCAGGCTTGGCTGAGACGGACGGTAGACTTCCACCATGTACCGATCACATCCCA   1620

ACTCTGCATGGCCCCTGCTAAGGCTCAGGTATAACCTCACCTTCCCTGGCTCATCTTGGC   1680

CTTGGGGAGTTGCCTTTAGGCTTGAGTCCTCAAGCCTCTCCTTTTCGTCCATAATAAAAT   1740

GGGAATTC                                                       1748
```

FIG. 7C

RECOMBINANT KAT ENZYME AND PROCESS FOR ITS PREPARATION

This is a continuation in part of Ser. No. 08/271,667 filed Jul. 7, 1994 now U.S. Pat. No. 5,817,496.

FIELD OF THE INVENTION

The present invention relates to DNA sequences that code for kynurenine aminotransferase.

BACKGROUND OF THE INVENTION

The enzyme kynurenine aminotransferase (known in the art as KAT) catalyzes the biosynthesis of kynurenic acid (KYNA) from kynurenine (KYN) and is singularly responsible for the regulation of extracellular KYNA concentrations in the brain (*J. Neurochem.*, 57:533–540 (1991)).

KYNA is an effective excitatory amino acid (EAA) receptor antagonist with a particularly high affinity to the glycine modulatory site of the N-methyl-D-aspartate (NMDA) receptor complex (*J. Neurochem.*, 52:1319–1328 (1989)). As a naturally occurring brain metabolite (*J. Neurochem.*, 51:177–180 (1988); and *Brain Res.*, 454:164–169 (1988)), KYNA probably serves as a negative endogenous modulator of cerebral glutamatergic function (*Ann. N.Y. Acad. Sci.*, 648:140–153 (1992)).

EAA receptors and in particular NMDA receptors are known to play a central role in the function of the mammalian brain (Watkins et al, *In: The NMDA Receptor*, page 242, (1989), Eds., Oxford University Press, Oxford). For example, NMDA receptor activation is essential for cognitive processes, such as, for example, learning and memory (Watkins et al, *In: The NMDA Receptor*, Eds., pages 137–151, (1989), Oxford University press, Oxford) and for brain development (*Trends Pharmacol. Sci.*, 11:290–296 (1990)).

It follows that a reduction in NMDA receptor function will have detrimental consequences for brain physiology and, consequently, for the entire organism. For example, the decline in the number of NMDA receptors which occurs in the aged brain (*Synapse*, 6:343–388 (1990)) is likely associated with age-related disorders of cognitive functions.

In the brain, KYNA concentrations and the activity of KYNA's biosynthetic enzyme KAT show a remarkable increase with age (*Brain Res.*, 558:1–5, (1992); and *Neurosci. Lett.*, 94:145–150 (1988)). KAT inhibitors, by providing an increase of the glutamatergic tone at the NMDA receptor, could therefore be particularly useful in situations where NMDA receptor function is insufficient and/or KAT activity and KYNA levels are abnormally enhanced. Hence they could be particularly useful in the treatment of the pathological consequences associated with the aging processes in the brain which are, for example, cognitive disorders including, e.g., attention and memory deficits and vigilance impairments in the elderly.

KAT inhibitors may also be useful in the treatment of perinatal brain disorders which may be related to irregularities in the characteristic region specific pattern of postnatal KAT development (Baran et al, *Dev. Brain Res.*, 74:283–286 (1993)).

In subcellular fractionation studies KAT activity was recovered in the cytosol and in mitochondria (*J. Neurochem.*, supra).

Most nuclear-encoded precursors of mitochondrial proteins contain amino-terminal presequences (Pfanner et al, *In: Current Topics in Bioenergetics*, 15:177–219 (1987); Lee Ed., New York Academic Press; and Nicholson et al, *In: Protein Transfer and Organelle Biogenesis*, Das and Robins Eds., New York Academic Press (1988)). These presequences are required for the precursor to enter the mitochondrial matrix, where they are proteolytically removed (Hurt et al, *FEBS Lett.*, 178:306 (1984); Horwich et al, *EMBO J.*, 4:1129 (1985). This cleavage is not essential for completing import but is necessary for further assembly of the newly imported polypeptides into functional complexes (Zwizinski et al, *J. Biol. Chem.*, 258:13340 (1983); Lewin et al, *J. Biol. Chem.*, 258:6750 (1983); Ou et al, *J. Biochem.*, 100:1287 (1986)). Precursor targeting sequences differ considerably in their structures. One of the few common themes is the high content of positively charged amino acids and of hydroxylated amino acids. Presequences may form an amphipathic structure in the form of either α-helices or β-sheets (von Heijne et al, *EMBO J.*, 5:1335 (1986); Roise et al, *EMBO J.*, 5:1327 (1986); and Vassarotti et al, *EMBO J.*, 6:705 (1987)). Despite the large variability of the sequences of mitochondrial leader peptides, relatively minor alterations of the presequence can prevent cleavage by the processing peptidase (Hurt et al, *J. Biol. Chem.*, 262:1420 (1987)). This suggests that distinct, but up to now undefined, structural elements are required for cleavage. Similarly, the cleavage sites show wide variation among different precursors of a single organism and among precursors of different organisms.

Interestingly, using the protein algorithm described by Gavel et al (*Protein Engineering*, 4:33–37 (1990)), a potential mitochondrial transit peptide is predicted either in position 1 to 24 of the deduced protein of cDNA-2 and in position 1 to 44 of the deduced protein of cDNA-3 disclosed in the present invention (see FIGS. 3–4 and Example 3). Recently Perry et al (*Mol. Pharm.*, 43:660–665 (1993)) reported the cloning of a cDNA coding for rat kidney cytosolic cysteine conjugate β-lyase.. When the cDNA was inserted into the expression vector PVS1000 and transfected into COS-1 tissue culture cells, a 7–10 fold increase in cytosolic β-lyase and glutamine transaminase K activities was detected. The deduced amino acid sequence of rat β-lyase is identical to the deduced amino acid sequence of cDNA-1 (rat KAT) except for two residues (see FIG. 2). Moreover the existence of cDNA-2 and cDNA-3 was not reported by Perry et al (*Mol. Pharm.*, supra).

Even more recently Perry et al (*FEBS Lett.*, 360:277–280 (1995)) reported the cloning of a cDNA for human kidney cysteine conjugate beta-lyase whose sequence is identical to the sequence of the human KAT described in the present patent application. Whereas the identity with cysteine conjugate β-lyase and glutamine transaminase K is well documented (Abraham et al, *Analytical Biochem.*, 197:421–427 (1991)), there are no reports indicating identity of kynurenine transaminase with either β-lyase or glutamine transaminase K.

SUMMARY OF THE INVENTION

We now report the cloning of mammalian kynurenine aminotransferases.

A first aspect of the present invention relates to isolated DNA sequences encoding a KAT enzyme selected from the group consisting of: (a) isolated DNA sequences which encode rat KAT; (b) an isolated DNA sequence which hybridizes to isolated DNA sequences of (a) above and which encodes a mammalian KAT enzyme; and (c) an isolated DNA sequence differing from the isolated DNA sequences of (a) and (b) above in codon sequence due to the degeneracy of the genetic code, and which encodes a KAT enzyme.

A second aspect of the present invention relates to vectors comprising a cloned DNA sequence as given above.

A third aspect of the present invention are host cells transformed with a vector as given above.

A fourth aspect of the present invention is an oligonucleotide probe capable of selectively hybridizing to a DNA comprising a portion of a gene coding for a KAT enzyme.

A fifth aspect of the present invention is isolated and purified KAT enzyme which is coded for by a DNA sequence selected from the group consisting of: (a) isolated DNA sequences which encode rat KAT; (b) an isolated DNA sequence which hybridizes to an isolated DNA sequence of (a) above and which encodes a mammalian KAT enzyme; and (c) an isolated DNA sequence differing from the isolated DNA sequences of (a) and (b) above in codon sequence due to the degeneracy of the genetic code, and which encodes a KAT enzyme.

BRIEF DESCRIPTION OF THE DRAWINGS

FIG. 1 Partial amino acid sequence of rat KAT: N-terminus of mature KAT (SEQ ID NO:14), a CNBr fragment (SEQ ID NO:15), tryptic fragment 112 of KAT (SEQ ID NO:16) and tryptic fragment 130 of KAT (SEQ ID NO:17).

FIGS. 2A–2C nucleotide sequence and deduced amino acid sequence of rat KAT (cDNA-1) (SEQ ID NO:18). The putative pyridoxal phosphate binding site, Ser—Ala—Gly—Lys—Ser—Phe, is underlined. Triplets differing from rat β-lyase cDNA (Perry et al, supra) are boxed.

FIGS. 3A–3D nucleotide sequence and deduced amino acid sequences of rat KAT (cDNA-2) (SEQ ID NO:19). Two proteins can be synthesized: one starting from nucleotide 619 and including a putative mitochondrial targeting peptide, the other beginning at the same ATG starting codon as in the case of cDNA-1. The putative pyridoxal phosphate binding site, Ser—Ala—Gly—Lys—Ser—Phe, is underlined. Triplets differing from rat β-lyase CDNA (Perry et al, supra) are boxed.

FIGS. 4A–4D nucleotide sequence and deduced amino acid sequences of rat KAT (cDNA-3) (SEQ ID NO:5). The sequence of cDNA-3 is identical to that of CDNA-1 except for an insertion of 208 base pairs in the 5'-untranslated region. The insertion creates an additional stretch of 34 amino acids in frame with the cDNA-1 deduced protein sequence. The insertion of these 208 base pairs occurs between nucleotide 237 and 238 of the cDNA-1 sequence.

FIG. 6 Partial amino acid sequence of human KAT I: tryptic fragments F11 (SEQ ID NO:2); F13 (SEQ ID NO:3); and F14 (SEQ ID NO:4) of the human KAT I.

FIGS. 7A–7C nucleotide sequence and deduced amino acid sequence of human KAT I (SEQ ID NO:1).

DETAILED DESCRIPTION OF THE INVENTION

Figure 5A:
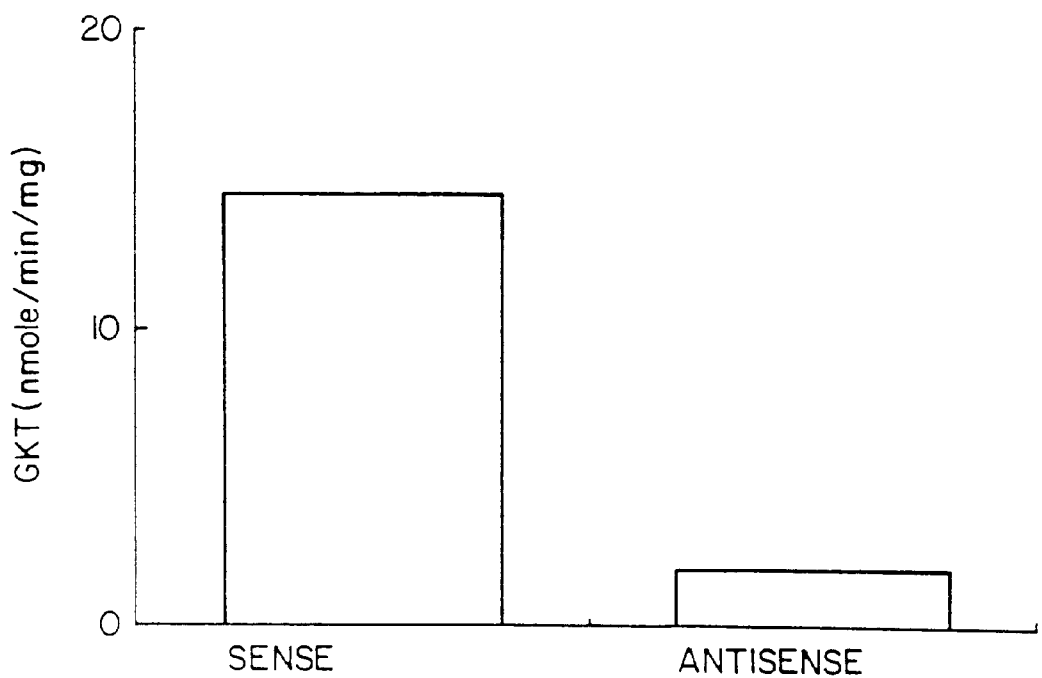
FIGS. 5A and 5B cytosolic enzyme activities in transfected COS-1 cells: 5A, glutamine transaminase K activity; 5B, kynurenine transaminase activity. Sense: pSVL-KAT transfected COS-1 cells where cDNA-1 is in the sense orientation. Antisense: PSVL-KAT transfected COS-1 cells were cDNA-1 is in reverse orientation. Each value is the mean of three separate experiments.
Figure 5B:
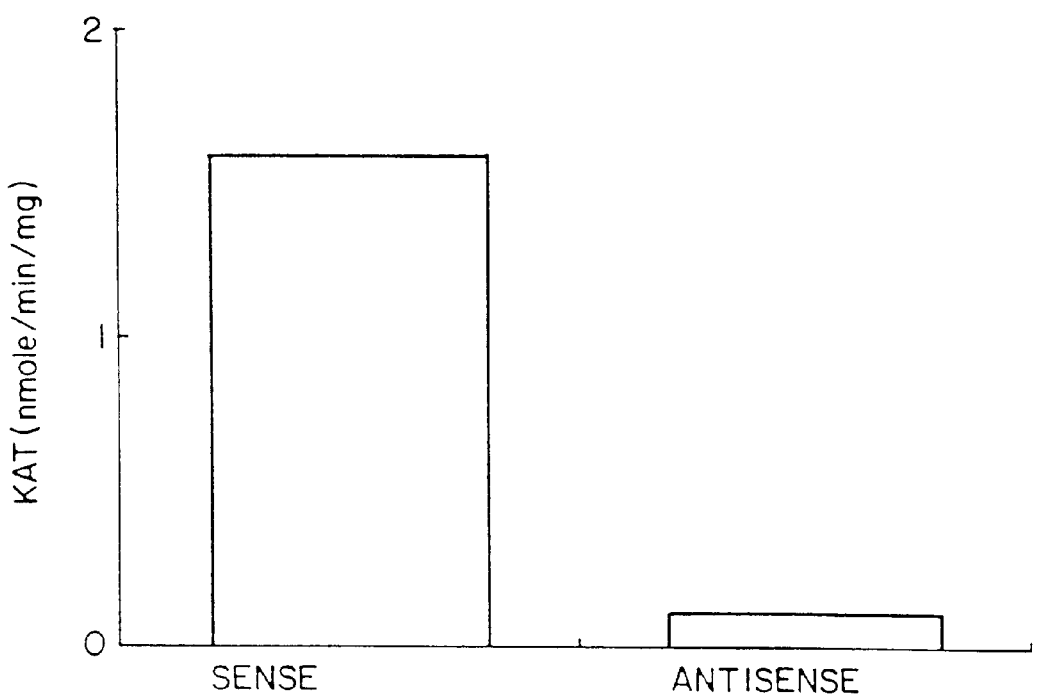

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code.

The kynurenine aminotransferase enzyme of the present invention includes proteins homologous to, and having essentially the same biological properties as, the protein coded for by the nucleotide sequences herein disclosed. This definition is intended to encompass natural allelic variants of KAT sequence.

Cloned genes of the present invention may code for KAT of any species of origin, but preferably code for enzymes of mammalian origin. Thus, DNA sequences which hybridize to the sequences given in FIGS. 2A–2C (SEQ ID NO:18), 3A–3D (SEQ ID NO:19), 4A–4D (SEQ ID NO:5) and 7A–7C (SEQ ID NO:1) and which code for expression of KAT are also an aspect of this invention. Conditions which will permit other DNA sequences which code for expression of KAT to hybridize to the sequences given in FIGS. 2A–2C (SEQ ID NO:18), 3A–3D (SEQ ID NO:19), 4A–4D (SEQ ID NO:5) and 7A–7C (SEQ ID NO:1) can be determined in a routine manner. Further, DNA sequences which code for polypeptides coded for by the sequences given in FIGS. 2A–2C (SEQ ID NO:18), 3A–3D (SEQ ID NO:19), 4A–4D (SEQ ID NO:5) and 7A–7C (SEQ ID NO:1) or sequences which hybridize thereto and code for a KAT enzyme, but which differ in codon sequence from these due to degeneracy of the genetic code, are also an aspect of this invention. The degeneracy of the genetic code, which allows different nucleic acid sequences to code for the same protein or peptide, is well known in the literature. See, e.g., Toole et al, U.S. Pat. No. 4,757,006 at column 2, Table 1.

DNA which encodes the KAT enzyme may be obtained by a variety of means well known to the expert in the art and disclosed by, for example, Maniatis et al, *Molecular Cloning: A Laboratory Manual,* 2nd Ed., Cold Spring Harbor Press, Cold Spring Harbor, N.Y. (1989).

For example, DNA which encodes the KAT enzyme may be obtained by screening of mRNA or genomic DNA with oligonucleotide probes generated from the KAT enzyme gene sequence information provided herein. Probes may be labeled with a detectable group such as a fluorescent group, a radioactive atom or a chemiluminescent group in accordance with known procedures and used in conventional hybridization assays, as described by, for example, Maniatis et al, supra.

KAT gene sequences may alternatively be recovered by use of the polymerase chain reaction (PCR) procedure, with the PCR oligonucleotide primers described herein or with oligonucleotide primers being produced from the KAT enzyme sequences provided herein. See Mullis et al, U.S. Pat. No. 4,683,195; and Mullis, U.S. Pat. No. 4,683,202. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

The recombinant DNA molecules of the present invention can be produced through any of a variety of means well known to the expert in the art and disclosed by, for example, Maniatis et al, supra. In order to replicate the KAT enzyme DNA sequences, these must be cloned in an appropriate vector. A vector is a replicable DNA construct. Vectors are used herein either to amplify DNA encoding the KAT enzyme and/or to express DNA which encodes the KAT enzyme. An expression vector is a replicable DNA construct in which a DNA sequence encoding the KAT enzyme is operably linked to suitable control sequences capable of effecting the expression of the KAT enzyme in a suitable host. DNA regions are operably linked when they are functionally related to each other. For example: a promoter is operably linked to a coding sequence if it controls the transcription of the sequence. Amplification vectors do not require expression control domains. All that is needed is the ability to replicate in a host, usually conferred by an origin of replication, and a selection gene to facilitate recognition of transformants.

DNA sequences encoding the KAT enzyme may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Maniatis et al, supra and are well known in the art.

Expression of the cloned sequence occurs when the expression vector is introduced into an appropriate host cell. If a prokaryotic expression vector is employed, then the appropriate host cell would be any prokaryotic cell capable of expressing the cloned sequences, for example E. coli. Similarly, if an eukaryotic expression vector is employed, then the appropriate host cell would be any eukaryotic cell capable of expressing the cloned sequence. A yeast host may be employed, for example S. cerevisiae. Alternatively, insect cells may be used, in which case a baculovirus vector system may be appropriate. Another alternative host is a mammalian cell line, for example COS-1 cells.

The need for control sequences into the expression vector will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Vectors useful for practicing the present invention include plasmids, viruses (including phages), retroviruses, and integratable DNA fragments (i.e., fragments integratable into the host genome by homologous recombination). The vectors replicate and function independently of the host genome, or may, in some instances, integrate into the genome itself.

Expression vectors should contain a promoter which is recognized by the host organism. The promoter sequences of the present invention may be either prokaryotic, eukaryotic or viral. Example of suitable prokaryotic sequences include the $P_R$ and $P_L$ promoters of bacteriophage lambda (Hershey, The Bacteriophage Lambda, Ed., Cold Spring Harbor Press, Cold Spring Harbor, N.Y. (1973); and Hendrix, Lambda II, Ed., Cold Spring Harbor Press, Cold Spring Harbor, N.Y. (1980)); the trp, recA, heat shock, and lacZ promoters of E. coli and the SV40 early promoter. (Benoist et al, Nature, 290:304–310 (1981)).

As far as the Shine-Dalgarno sequence is concerned, preferred examples of suitable regulatory sequences are represented by the Shine-Dalgarno of the replicase gene of the phage MS-2 and of the gene cII of bacteriophage lambda. The Shine-Dalgarno sequence may be directly followed by the DNA encoding KAT and result in the expression of the mature KAT protein.

Alternatively, the DNA encoding KAT may be preceded by a DNA sequence encoding a carrier peptide sequence. In this case, a fusion protein is produced in which the N-terminus of KAT is fused to a carrier peptide, which may help to increase the protein expression levels and intracellular stability, and provide simple means of purification. A preferred carrier peptide includes one or more of the IgG binding domains of Staphylococcus protein A. Fusion proteins comprising IgG binding domains of protein A are easily purified to homogeneity by affinity chromatography, e.g., on IgG-coupled Sepharose. A DNA sequence encoding a recognition site for a proteolytic enzyme such as enterokinase, factor X or procollagenase may immediately precede the sequence for KAT to permit cleavage of the fusion protein to obtain the mature KAT protein.

Moreover, a suitable expression vector includes an appropriate marker which allows the screening of the transformed host cells. The transformation of the selected host is carried out using any one of the various techniques well known to the expert in the art and described in Maniatis et al, supra.

One further embodiment of the invention is a prokaryotic host cell transformed with the said expression vector and able to produce, under appropriate culture conditions, the KAT of the invention.

Cultures of cells derived from multicellular organisms are a desirable host for recombinant KAT synthesis. In principal, any eukaryotic cell culture is workable, whether from vertebrate or invertebrate culture, including insect cells. Propagation of such cells in cell culture has become a routine procedure. See Kruse et al, Tissue Culture, Eds., Academic Press (1973). Examples of useful host cell lines are HeLa cells, CHO and COS cell lines. The transcriptional and translational control sequences in expression vectors to be used in transforming vertebrate and invertebrate cells are often provided by viral sources. For example, commonly used promoters are derived from Adenovirus 2, polyoma and SV40. See, e.g. U.S. Pat. No. 4,599,308.

An origin of replication may be provided either by construction of the vector to include an exogenous origin or may be provided by the host cell chromosomal replication mechanism. If the vector is integrated into the host cell chromosome, the latter may be sufficient.

Rather than using vectors which contain viral origins of replication, one can transform mammalian cells by the method of cotransformation with a selectable marker and the KAT DNA. An example of a suitable marker is dihydrofolate reductase (DHFR) or thymidine kinase. See U.S. Pat. No. 4,399,216.

Cloned genes and vectors of the present invention are useful to transform cells which do not ordinarily express KAT to thereafter express this enzyme. Such cells are useful as intermediates for making recombinant KAT preparations useful for drug screening.

Moreover, genes and vectors of the present invention are useful in gene therapy. For such purposes, adenovirus vectors as well as retroviral vectors as described in Temin et al, U.S. Pat. No. 4,650,764 and Miller, U.S. Pat. No. 4,861,719 may be employed.

Cloned genes of the present invention, and oligonucleotides derived therefrom, are useful for screening for restriction fragment length polymorphism (RFLP) associated with certain disorders.

Oligonucleotides of the present invention are useful as diagnostic tools for probing KAT gene expression in various tissues. For example, tissue can be probed in situ with oligonucleotide probes carrying detectable groups by conventional autoradiography techniques to investigate native expression of this enzyme or pathological conditions relating thereto.

Genetically modified (transfected) cells have been successfully used for cerebral implantation. Cells transfected with the KAT gene can be useful for delivering kynurenic acid (or any other KAT product; see below) to the brain. This may prove to be an attractive means to circumvent the blood-brain barrier for kynurenic acid through peripheral administration of kynurenine (or any appropriate substrate of KAT; see below).

Transfected cells expressing large quantities of KAT are also useful for the production of neuroactive kynurenic analogs. For example, KAT is capable of forming the potent NMDA receptor antagonist and neuroprotectant 7-chlorokynurenic acid from its bioprecursor L-4-chlorokynurenine (*J. Med. Chem.*, 37:334–336 (1994)).

The present invention is explained in greater detail in the following examples. These examples are intended to be illustrative of the present invention, and should not be constructed as limiting thereof.

EXAMPLE 1

Amino Acid Sequence of Tryptic Fragments of the Rat KAT

Protein Purification

Rat KAT was prepared essentially as described by Okuno et al, *Brain Res.*, 534:37–44 (1990). The enzyme eluted from a Sephacryl S-200 column was separated by HPLC on a reverse-phase column (SC18, 250×4.6 mm, Japan Spectro. Co. Ltd). Elution was performed with a gradient of solvent A (70% vol/vol) acetonitrile in 0.1% trifluoroacetic acid (TFA)) and solvent B (0.1% TFA) applied for 40 min at a flow rate of 1 ml/min.

Trypsin and CNBr Digestion and Fragment Purification 500 pmoles of HPLC-purified rat KAT sample were digested by trypsin as described (Hugli, *In: Techniques In Protein Chemistry*, Eds., Academic Press, Inc., pages 377–391 (1989)) and by CNBr. These samples were subjected to reverse-phase HPLC after digestion and the resulting peaks collected.

Amino Acid Sequence Analysis

Sequence analysis was performed essentially as described (Fabbrini et al, *FEBS Lett.*, 286:91–94 (1991)). FIG. 1 shows the partial amino acid sequence of rat KAT: N-terminus of mature KAT, (SEQ ID NO:14) a CNBr fragment (SEQ ID NO:15), tryptic fragment 112 of KAT (SEQ ID NO:16) and tryptic fragment 130 of KAT (SEQ ID NO:17).

EXAMPLE 2

Polymerase Chain Reaction (PCR) Cloning

RNA extraction

Total RNA from rat kidney was extracted from small quantities of tissue according to the instruction of RNAzol™ method (RNAzol-Cinna/Biotex Lab., Tex., U.S.A.).

First Strand cDNA Synthesis

First strand CDNA was synthesized from 3 mg of total RNA using 2 mg oligo polydT (18 pb), 4 ml of dNTP (2.5 mM), 8 ml of AMV buffer (TrisHCl pH8.8 250 mM/ KCl 200 mM/MgCl$_2$ 50 mM/ DTT 20 mM) in a final volume of 38.75 ml. The solution was boiled for 3 min at 65° C. and then placed on ice for 10 min; 0.75 ml of RNAsin (40 μ/ml Promega) and 0.5 ml of AMV Reverse transcriptase (25 μ/ml Boehringer Mannheim,GmbH, Germany) were added to the cold solution. The reaction was carried on at 42° C. for 2 h.

Design and Synthesis of Degenerated Oligonucleotides

Since the relative position of tryptic fragments 112 and 130 along the rat KAT primary structure was unknown, four degenerated oligonucleotides each 26 bp, were designed and synthesized using a DNA/RNA synthesizer (380B Applied Biosystems). The product of the reactions was purified on Sephadex G50 (Nap 25 Column, Pharmacia).

The sense orientation oligonucleotide, OligoA: (AAYYTNTGYCARCARCAYGAYGTNGT) (SEQ ID NO:20), and the anti-sense orientation oligonucleotide, OligoC: (ACNACRTCRTGYTGYTGRCANARRTT) (SEQ ID NO:21), were based on the peptide sequence Asn—Leu—Cys—Gln—Gln—His—Asp—Val—Val (residues 7–15 of fragment 130 (SEQ ID NO:17)). The sense orientation oligonucleotide, OligoB: (ACNGANARRTTYTGRTCXATNCCRTC) (SEQ ID NO:22), and the corresponding anti-sense oligonucleotide, OligoD: (GAYGGNATZGAYCARAAYYTNTCNGT) (SEQ ID NO:23), were based on the peptide sequence Asp—Gly—Ile—Asp—Gln—Asn—Leu—Ser—Val (residues 3–11 of fragment 112 (SEQ ID NO:16)) (N=T/C/A/G; Z=T/C/A; R=A/G; Y=T/C; X=T/G/A).

Polymerase Chain Reaction Condition

The first strand CDNA was divided in two aliquots and amplified by PCR as described below. The two oligonucleotide mixtures PCR1: oligoA and oligoD and PCR2: OligoB and OligoC were used as primers in the PCR reactions. 70 ng of template CDNA were combined with 10 mg of each set of primers, 10 ml of 10× Taq polymerase buffer (500 mM KCl/100 mM Tris—HCl, pH 8.3), 8 ml of 25 mM MgCl$_2$, 8 ml of a dNTP solution (2.5 mM dNTP) and 0.5 ml (2.5 units) of Taq DNA polymerase (Perkin Elmer Cetus). The volume was brought to 100 ml with H$_2$O and the mixture was overlayed with mineral oil to prevent evaporation. The tube was heated to 94° C. for 3 min, denaturation was carried out for 3 minutes at 94° C., annealing for 2 min at 60° C. and polymerization for 2 min and 30 seconds at 72° C. The cycle was repeated 30 times.

A specific amplification product was observed only with PCR1. The product of the amplification was a DNA molecule of about 550 bp. The PCR1-amplification product was re-amplified using a new set of oligos, basically with the same sequence of oligoA and oligoc with SalI linkers and 5'-extra nucleotides. OligoE: (GCTA-GTCGACACNACRTCRTGYTGYTGRCANARRTT) (SEQ ID NO:24) complementary to nucleotides coding for peptide 130 (SEQ ID NO:17) and OligoF: (GATCGTCGACGAYGGNATZGAYCARAAYYTNT-CNGT) (SEQ ID NO:25) corresponding to nucleotides coding for peptide 112 (SEQ ID NO:16).

After PCR amplification, the resulting DNA fragment was digested overnight with the restriction enzyme SalI and ligated into the SalI site of the cloning plasmid pUC18 (Yanisch-Perron et al, *Gene*, 33:103–119 (1985)). The recombinant plasmid was extracted according to the instruction of the Qiagen Plasmid Maxi Protocol, precipitated with PEG, and denatured with NaOH 2 N.

Sequencing was carried out with universal and forward primers and subsequently with a series of synthetic oligonucleotide primers according to the dideoxy chain termination method (Sanger et al, *Proc. Natl. Acad. Sci. USA*, 74:5463–5467 (1977)) using Sequenase (United States Biochemicals Corp., Cleveland, Ohio).

Both strands of the insert were sequenced revealing an open reading frame of 196 amino acids. Part of the two rat KAT peptides that were sequenced are encoded by the corresponding 588 bp open reading frame. This open reading frame is used as probe in the cDNA library screening described in Example 3.

EXAMPLE 3 cDNA Library Screening

About 500,000 recombinant phages of λgt11 rat kidney CDNA library (Clontec Laboratories, USA) were plated on a lawn of *E. coli* Y1090 cells. After an overnight growth at 37° C. the recombinant phages were transferred to duplicate nitrocellulose filters; their DNA was then denatured, neutralized and baked under vacuum at 80° C. for 2 h. Prehybridization was carried out at 60° C. for 4 h in 6×SSC, 5× Denhardt's, 1% SDS, 200 μg/ml salmon sperm DNA. The filters were then hybridized overnight at 60° C. in the same mixture with the addition of about $1.5 \times 10^6$ cpm/ml of labeled probe (see Example 2).

The probe was labeled with ($^{32}$p) dCTP by Multiprime DNA labeling system (Amersham), purified on Nick Column (Pharmacia) and added to the hybridizing solution.

The filters were washed at 60° C. twice in 2×SSC, 0.1% SDS and once in 1×SSC, 1% SDS. Filters were exposed to Kodak X-AR film (Eastman Kodak Company, Rochester, N.Y., USA) with intensifying screen at −80° C.

Positive phage plaques were isolated and screened again twice in order to isolate single clones.

Recombinant Phage DNA Extraction and Sequencing Methods

About 50,000 phages of each positive clone were plated on a lawn of *E. coli* Y1090 cells. After an overnight growth at 37° C., phages were resuspended in SM buffer (100 mM NaCl/8 mM MgSO$_4$/50 mM Tris—HCl, pH 7.5/gelatin 0.001%) and chloroform 0.3%; the suspension was treated with 1 mg of RNAse and 1 mg of DNAse. Phage DNA was precipitated with PEG 10%/1 M NaCl, extracted with phenol and phenol:chloroform:iso-amyl alcohol and precipitated with PEG again.

The phage DNA was digested with EcoRI and the insert was ligated to the EcoRI site of pUC18.

The recombinant plasmid was extracted according to the instruction of Qiagen Plasmid Maxi Protocol; precipitated with PEG and denatured with 2 N NaOH.

Sequencing was carried out with universal and forward primers and subsequently with a series of synthetic oligonucleotide primers according to dideoxy chain termination method (Sanger et al, supra) using Sequenase (United States Biochemicals Corp., Cleveland, Ohio).

Three positive clones were isolated, cDNA-1, cDNA-2 and cDNA-3. Both strands of the three cDNAs were sequenced (see FIGS. 2A–2C, 3A–3D and 4A–4D).

cDNA-1 encodes a deduced protein of 423 amino acid residues, cDNA-2 encodes a deduced protein of 437 amino acid residues and cDNA-3 encodes a deduced protein of 457 amino acid residues.

The three deduced proteins differ only in their N-terminus. Moreover, the cDNA-2 and cDNA-3 clones are not homogeneous, since an alternative 5' sequence introduces an upstream ATG starting codon.

As already said, the longer proteins deduced from the cDNA-2 and cDNA-3 clones present a putative mitochondrial transit peptide in position 1 to 24 (cDNA-2) and in position 1 to 44 (cDNA-3) which is only partially present in the 423 amino acid protein.

EXAMPLE 4

Cloning of human KAT

A λ ZapII human brain CDNA library (Stratagene) was screened with a probe representing the N-terminal part of the cDNA-1, encompassing a sequence from amino acid residue 11 to 197 and encoding rat kidney KAT. About 1,350,000 recombinant phages were plated on a lawn of *E. coli* XL1 blue cells and screening was performed as described in the Example 3.

Positive phage plaques were isolated and screened again twice in order to isolate single clones.

Recombinant Phage DNA Extraction and Sequencing Methods

*E. coli* XL1 blue cells were coinfected with about $10^5$ phage particles corresponding to the positive clone selected and 1 μl of EX Assist helper phage ($10^6$ pfu/ml). The mixture was incubated at 37° C. for 15 min and later incubated with 3 ml of LB for 3 h. Cells were spun down and the supernatant was heated 70° C. for 15 min. SORL cells at OD600=1 were mixed with the supernatant containing the phagemid pBluescript and incubated for 15 min at 37° C. and plated on LB-ampicillin plates (50 μg/ml). Single clones were incubated overnight in LB-ampicillin and DNA was extracted according to the instruction of the Qiagen Plasmid Maxi Protocol, then precipitated with PEG and denaturaed with NaOH 2 N. Sequencing was carried out with universal and forward primer and subsequently with a series of synthetic oligonucleotide primers according to the dideoxy chain termination method (Sanger et al, supra) using Sequenase (United States Biochemicals Corp., Cleveland, Ohio).

Unfortunately none of the positive clones contained a full length sequence. Therefore, in order to isolate the 5' missing sequence, a RACE protocol was performed.

5' PCR Race 0.5 μg of polyA+RNA from human brain was reverse transcribed with a primer (5'-CAGGGCCTGGAAGGCTGTGA-3') (SEQ ID NO:6) located at the N-terminal part of the longest cDNA clone isolated from the human brain cDNA library. Reaction was carried out as described in Example 2. 20 μl of the product was precipitated and resuspended in a mixture containing DATP 0.2 mM, buffer tailing (0.1 M potassium cacodylate pH 6.8, 1 mM CoCl$_2$, 100 mM DTT, 100 μg/ml BSA) and 15 U TdT enzyme (Gibco BRL). After incubation at 37° C. for 10 min, water was added to a final reaction volume of 250 μl. CDNA was mixed with 25 pmol of oligo (5'-ATAGCCACCAACAGTCACCA-3') (SEQ ID NO:7), 10 pmol of oligo (5'-GACTCGAGTCGACATCGATTTTTTTTTTTTTTTT-3') (SEQ ID NO:8) and 25 pmol of oligo (5'-GACTCGAGTCGACATCGA-3') (SEQ ID NO:9), 10 μl of 10× Taq polymerase buffer (500 mM KCl/100 mM Tris—HCl, pH 8.3), 8 μl of 25 mM MgCl$_2$, 8 μl of a dNTP solution (2.5 mM dNTP). The volume was brought to 100 μl with H$_2$O. The tube was heated at 95° C. for 7 min and 0.5 μl (2.5 U) of Taq polymerase (Perkin Elmer Cetus) were added. Annealing was carried out for 2 min at 58° C. and polymerization for 2.5 min at 72° C. The cycle was repeated 40 times. PCR products were blotted on a nitrocellulose filter and hybridized as described in Example 3 with a oligonucleotide probe (5'-ACCACTGA-CGAAGATCCTGGCAAGTTTCTTTGGGGAGC-3') (SEQ ID NO:10), based on the known sequence of the partial CDNA human clone. Probe was labeled with (λ$^{32}$p) dATP by T4 polynucleotide Kinase (Boehringer) and purified on a Nap5 column (Pharmacia). A positive band (330 bp), termed 5'-hKAT, was re-amplified using an oligo with SalI linkers then cloned in pUC18. DNA sequencing was performed on both strands confirming correspondence between the PCR fragment and the missing 5'-part of the human KAT clone.

EXAMPLE 5

Expression in Mammalian Cells

The expression plasmid encoding rat KAT was constructed as follows: to remove the 5' and the 3' untranslated sequences, as well as the putative mitochondrial targeting peptide, PCR amplification was performed using two specific oligonucleotides with XhoI linkers. The sense orientation oligonucleotide (5'-TGTCCTC-GAGACCATGACCAAACGGCTGCAGGCTCGGA-3') (SEQ ID NO:26) begins at +241 of cDNA-1, whereas the antisense-orientation oligonucleotide (5'-GTACCTCGAGTCAGGGTTGGAGCTCTTTCCACTTG-3') (SEQ ID NO:27) complements the sequence starting from the end of the coding sequence. The XhoI-digested fragment, after being confirmed by sequencing, was cloned into the XhoI site of pSVL expression vector (Pharmacia Biotechnology).

The expression plasmid encoding human KAT was constructed as follows. In order to join the two cDNA fragments corresponding to the full length sequence of human KAT, two different PCR reactions were carried out. 5' hKAT was amplified by PCR using two specific oligonucleotides: a sense primer with XhoI linker (TGTCCTCGAGACCATGGCCAAACAGCTC) (SEQ ID NO:11) and as reverse primer (CAGGGCCTGGAAGGCTGTGA) (SEQ ID NO:6) the oligonucleotide used for the reverse transcription of Race (see Example 4). The partial CDNA sequence coding for human KAT obtained after cDNA library screening (Example 4) was PCR amplified using two primers flanking the cloning site: sense primer (GTAATACGACTCACTATAGGGC) (SEQ ID NO:12) and reverse primer (TGTCCTCGAGCGCTCTAGAACTAGTGGATC) (SEQ ID NO:13). The two PCR product were were digested with ApaI, linked together, digested XhoI and cloned into the PSVL vector. COS-1 cells were transfected with 10 μg of pSVL-ratKAT plasmid or pSVL-humanKAT by the calcium phosphate method (Maniatis et al, supra). 72 h after transfection, cells were disrupted by freezing and thawing, and after centrifugation, the supernatant was tested for KAT, glutamine transaminase K and cysteine conjugate β-lyase activities.

EXAMPLE 6

Kynurenine Amino Transferase, Glutamine Amino Transferase K and Cysteine Conjugate β-lyase Activities Kynurenine transaminase assay The reaction mixture (100 μl) contained 70 μM pyridoxal phosphate, 5 mM pyruvate, 3 mM kynurenine, and KAT sample in 0.17 M potassium phosphate buffer, pH 8.1, and was incubated at 37° C. for 1 h and 30 min. Reaction was stopped by adding 20 μl TCA 50% and the precipitate was removed by centrifugation. The supernatant was analyzed by HPLC with a C18 column (Vydac 201TP54, 25×4.6 cmxmm) at 1 ml/min, equilibrated with 5 mM acetic acid, 5% methanol, 0.1% heptane sulfonic acid, pH 3.0; kynurenic acid was eluted with 50mM acetic acid, 5% methanol, 0.5% heptane sulfonic acid, pH 4.5. Absorbance at 243 nm was measured.

Glutamine Transaminase K Assay

Glutamine transaminase K activity was measured as described by Cooper and Meister (Methods Enzymol., 113:344–349 (1985)).

Cysteine Conjugate β-lyase Assay

The β-lyase assay was a coupled assay as described by Abraham and Cooper (1991). The product of the β-lyase reaction (pyruvate) was assayed by measuring the oxidation of NADH during the transformation of pyruvate to lactate catalyzed by alanine dehydrogenase. The reaction mixture (200 ml in a microtiter plate) contained 2 mM S-(1,2-dichlorovinyl)-L-cysteine (DCVC), 0.5 mM MTB, 0.1 mM PLP and the enzyme in 100 mM Tris buffer pH 8.8, and was incubated at 37° C. for 5, 10, 15 min prior the addition of 0.3 mM NADH, 7.3 U/ml alanine dehydrogenase, and ammonium acetate 0.1 M. Absorbance at 340 nm was measured using a microplate reader (Cerves uv900) and NADH concentration was calculated using a $\epsilon l = 4200$ $M^{-1}$.

EXAMPLE 7

Amino Acid Sequence of Tryptic Fragments of the Human KAT

Human KAT was prepared essentially as described by Baran et al, J. Neurochem., 62:730–738 (1994).

500 pmoles of the purified human KAT sample were digested by trypsin as described (Hugli, In: Techniaues in Protein Chem., pages 377–391, Eds., Academic Press, Inc., (1989)). Briefly, human KAT was desalted using SMART system equipped with a Fast desalting column equilibrated in 10 mM ammonium bicarbonate. After the chromatography step, the sample was concentrated to a final volume of % ml. Cysteine residues in the molecule were reduced in 8 M urea, 10 mM DTT at 50° C. for 15 min then the alkylation was carried out with 20 mM iodoacetic acid for 15 min at room temperature. After this time the sample solution was diluted to have a final urea concentration of 2 M and the sample was digested overnight with trypsin (Boehringer) (enzyme:substrate ratio 1:25). Peptides resulting from digestion were analyzed by RP-HPLC using a Vydac C18 column and a linear gradient from 5 to 65% eluent B during 60 min, where eluent A was 0.1% trifluoroacetic acid (TFA) in water and eluent B was 0.07% TFA, 95% acetonitrile. Eluted peaks were manually collected, concentrated using a vacuum speedvac (Savant) and then loaded onto a 477 N-terminal protein sequencer (ABI, Perkin Elmer) for protein sequence determination.

Sequence analysis was performed essentially as described (Fabbrini et al, FEBS Lett., supra). FIG. 6 shows the amino acid sequence of three peptides of human KAT, namely F11 (SEQ ID NO:2), F13 (SEQ ID NO:3) and F14 (SEQ ID NO:4).

While the invention has been described in detail, and with reference to specific embodiments thereof, it will be apparent to one of ordinary skill in the art that various changes and modifications can be made therein without departing from the spirit and scope thereof.

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
       (A) LENGTH: 1748 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 1:

```
CT TAATGTTTTT AGAGCTCACC ATG GCC AAA CAG CTG CAG GCC CGA AGG           49
                        Met Ala Lys Gln Leu Gln Ala Arg Arg
                         1               5

CTA GAC GGG ATC GAC TAC AAC CCC TGG GTG GAG TTT GTG AAA CTG            94
Leu Asp Gly Ile Asp Tyr Asn Pro Trp Val Glu Phe Val Lys Leu
 10              15                  20

GCC AGT GAG CAT GAC GTC GTG AAC TTG GGC CAG GGC TTC CCG GAT           139
Ala Ser Glu His Asp Val Val Asn Leu Gly Gln Gly Phe Pro Asp
 25              30                  35

TTC CCA CCA CCA GAC TTT GCC GTG GAA GCC TTT CAG CAC GCT GTC           184
Phe Pro Pro Pro Asp Phe Ala Val Glu Ala Phe Gln His Ala Val
 40              45                  50

AGT GGA GAC TTC ATG CTT AAC CAG TAC ACC AAG ACA TTT GGT TAC           229
Ser Gly Asp Phe Met Leu Asn Gln Tyr Thr Lys Thr Phe Gly Tyr
 55              60                  65

CCA CCA CTG ACG AAG ATC CTG GCA AGT TTC TTT GGG GAG CTG CTG           274
Pro Pro Leu Thr Lys Ile Leu Ala Ser Phe Phe Gly Glu Leu Leu
 70              75                  80

GGT CAG GAG ATA GAC CCG CTC AGG AAT GTG CTG GTG ACT GTT GGT           319
Gly Gln Glu Ile Asp Pro Leu Arg Asn Val Leu Val Thr Val Gly
 85              90                  95

GGC TAT GGG GCC CTG TTC ACA GCC TTC CAG GCC CTG GTG GAC GAA           364
Gly Tyr Gly Ala Leu Phe Thr Ala Phe Gln Ala Leu Val Asp Glu
100             105                 110

GGA GAC GAG GTC ATC ATC ATC GAA CCC TTT TTT GAC TGC TAC GAG           409
Gly Asp Glu Val Ile Ile Ile Glu Pro Phe Phe Asp Cys Tyr Glu
115             120                 125

CCC ATG ACA ATG ATG GCA GGG GGT CGT CCT GTG TTT GTG TCC CTG           454
Pro Met Thr Met Met Ala Gly Gly Arg Pro Val Phe Val Ser Leu
130             135                 140

AAG CCG GGT CCC ATC CAG AAT GGA GAA CTG GGT TCC AGC AGC AAC           499
Lys Pro Gly Pro Ile Gln Asn Gly Glu Leu Gly Ser Ser Ser Asn
145             150                 155

TGG CAG CTG GAC CCC ATG GAG CTG GCC GGC AAA TTC ACA TCA CGC           544
Trp Gln Leu Asp Pro Met Glu Leu Ala Gly Lys Phe Thr Ser Arg
160             165                 170

ACC AAA GCC CTG GTC CTC AAC ACC CCC AAC AAC CCC CTG GGC AAG           589
Thr Lys Ala Leu Val Leu Asn Thr Pro Asn Asn Pro Leu Gly Lys
175             180                 185

GTG TTC TCC AGG GAA GAG CTG GAG CTG GTG GCC AGC CTT TGC CAG           634
Val Phe Ser Arg Glu Glu Leu Glu Leu Val Ala Ser Leu Cys Gln
190             195                 200

CAG CAT GAC GTG GTG TGT ATC ACT GAT GAA GTC TAC CAG TGG ATG           679
Gln His Asp Val Val Cys Ile Thr Asp Glu Val Tyr Gln Trp Met
205             210                 215
```

```
GTC TAC GAC GGG CAC CAG CAC ATC AGC ATT GCC AGC CTC CCT GGC      724
Val Tyr Asp Gly His Gln His Ile Ser Ile Ala Ser Leu Pro Gly
220             225                 230

ATG TGG GAA CGG ACC CTG ACC ATC GGC AGC GCC GGC AAG ACC TTC      769
Met Trp Glu Arg Thr Leu Thr Ile Gly Ser Ala Gly Lys Thr Phe
235             240                 245

AGC GCC ACT GGC TGG AAG GTG GGC TGG GTC CTG GGT CCA GAT CAC      814
Ser Ala Thr Gly Trp Lys Val Gly Trp Val Leu Gly Pro Asp His
250             255                 260

ATC ATG AAG CAC CTG CGG ACC GTG CAC CAG AAC TCC GTC TTC CAC      859
Ile Met Lys His Leu Arg Thr Val His Gln Asn Ser Val Phe His
265             270                 275

TGC CCC ACG CAG AGC CAG GCT GCA GTA GCC GAG AGC TTT GAA CGG      904
Cys Pro Thr Gln Ser Gln Ala Ala Val Ala Glu Ser Phe Glu Arg
280             285                 290

GAG CAG CTG CTC TTC CGC CAA CCC AGC AGC TAC TTT GTG CAG TTC      949
Glu Gln Leu Leu Phe Arg Gln Pro Ser Ser Tyr Phe Val Gln Phe
295             300                 305

CCG CAG GCC ATG CAG CGC TGC CGT GAC CAC ATG ATA CGT AGC CTA      994
Pro Gln Ala Met Gln Arg Cys Arg Asp His Met Ile Arg Ser Leu
310             315                 320

CAG TCA GTG GGC CTG AAG CCC ATC ATC CCT CAG GGC AGC TAC TTC     1039
Gln Ser Val Gly Leu Lys Pro Ile Ile Pro Gln Gly Ser Tyr Phe
325             330                 335

CTC ATC ACA GAC ATC TCA GAC TTC AAG AGG AAG ATG CCT GAC TTG     1084
Leu Ile Thr Asp Ile Ser Asp Phe Lys Arg Lys Met Pro Asp Leu
340             345                 350

CCT GGA GCT GTG GAT GAG CCC TAT GAC AGA CGC TTC GTC AAG TGG     1129
Pro Gly Ala Val Asp Glu Pro Tyr Asp Arg Arg Phe Val Lys Trp
355             360                 365

ATG ATC AAG AAC AAG GGC TTG GTG GCC ATC CCT GTC TCC ATC TTC     1174
Met Ile Lys Asn Lys Gly Leu Val Ala Ile Pro Val Ser Ile Phe
370             375                 380

TAT AGT GTG CCA CAT CAG AAG CAC TTT GAC CAC TAT ATC CGC TTC     1219
Tyr Ser Val Pro His Gln Lys His Phe Asp His Tyr Ile Arg Phe
385             390                 395

TGT TTT GTG AAG GAT GAA GCC ACG CTC CAG GCC ATG GAC GAG AAG     1264
Cys Phe Val Lys Asp Glu Ala Thr Leu Gln Ala Met Asp Glu Lys
400             405                 410

CTG CGG AAG TGG AAG GTG GAA CTC TAGCCCTGAA GTCACGCCTT           1308
Leu Arg Lys Trp Lys Val Glu Leu
415             420

GGCCCTGACA TCCCCACATG CCCGCAGAGA TCCTCTTTGA GTGTCTGTCT          1358

TTGTCCAGGT TTCAGACATT TCTAGGTTGG GGAAGATGCT ATTGGGAAAC          1408

CTCTTCTCCG TGACACAGAA TGTTCTGGGT GGGAGCCGCC CTTCTTCATC          1458

TTAGAGAACC AAGTACCTCC TGTCTGAAAG GTGAGGGTGG CCTGACCTGG          1508

GCCTCTCCCT GCCCCTCCAT AGGTGGGTTT GTAGGGTCTT GTGTTGCTTC          1558

TGGTCTCTCC AGGCTTGGCT GAGACGGACG GTAGACTTCC ACCATGTACC          1608

GATCACATCC CAACTCTGCA TGGCCCCTGC TAAGGCTCAG GTATAACCTC          1658

ACCTTCCCTG GCTCATCTTG GCCTTGGGGA GTTGCCTTTA GGCTTGAGTC          1708

CTCAAGCCTC TCCTTTTCGT CCATAATAAA ATGGGAATTC                     1748

(2) INFORMATION FOR SEQ ID NO: 2:

(i) SEQUENCE CHARACTERISTICS:
```

(A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Thr Phe Ser Ala Thr Gly Xaa Lys
1               5

(2) INFORMATION FOR SEQ ID NO: 3:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Ala Leu Val Leu Asn Thr Pro Asn Asn Pro Leu Gly Lys
1               5                   10

(2) INFORMATION FOR SEQ ID NO: 4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Glu Gln Leu Leu Phe Arg
1               5

(2) INFORMATION FOR SEQ ID NO: 5:

(i) SEQUENCE CHARACTERISTICS:
        (A) LENGTH: 2101 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

| | |
|---|---:|
| AAACTGACCA AGGAGTATGA TCAATCCCGT CCAGCCTCCG AGCCTGCAGC | 50 |
| CGTTTGGTCA TGGTGAGCTG CTTCAGCTAA CAATTGCACT GACAGTGCTC | 100 |
| TTGAGCCAAG TTGCTTCTGG GCGGAAGTAG TCCATCTAGG GCTCGGCCTC | 150 |
| TTTAAAGAAA CAGACTTCTG CAACCTTGGG ACTACGTTTG GGGTCGCCGG | 200 |
| CTATTGGACG GAGCAGCGCA ATTGTTAGCT GAAGCAGAAC TGTGTGTGGA | 250 |
| CTCAGGCCCT GGCTTGGAGC CATTTTCTGG GCTAGGCTGT CTGCCCTTCT | 300 |
| GTCCCTCTGG AGGGGAAGCC TGCAGTGCCT GTGGACCTAC CTCAGAGGCA | 350 |
| TGTTCAGGAG TGCAGCAGCC CTCTCGGTGC ACCTGATGTG GCCACTCTGG | 400 |
| GGAAGGAAAG CTGGAGCCTC ACTCACCCGG TGCTTGCACC AGTCTCTCAC | 450 |
| C ATG ACC AAA CGG CTG CAG GCT CGG AGG CTG GAC GGG ATT | 490 |
|   Met Thr Lys Arg Leu Gln Ala Arg Arg Leu Asp Gly Ile | |
|   1           5                   10 | |

```
GAT CAA AAC CTC TGG GTG GAG TTT GGC AAA CTG ACC AAG GAG                532
Asp Gln Asn Leu Trp Val Glu Phe Gly Lys Leu Thr Lys Glu
    15                  20                  25

TAT GAC GTC GTG AAC TTG GGT CAG GGC TTC CCT GAC TTC TCG                574
Tyr Asp Val Val Asn Leu Gly Gln Gly Phe Pro Asp Phe Ser
        30                  35                  40

CCT CCG GAC TTT GCA ACG CAA GCT TTT CAG CAG GCT ACC AGT                616
Pro Pro Asp Phe Ala Thr Gln Ala Phe Gln Gln Ala Thr Ser
            45                  50                  55

GGG AAC TTC ATG CTC AAC CAG TAC ACC AGG GCA TTT GGT TAC                658
Gly Asn Phe Met Leu Asn Gln Tyr Thr Arg Ala Phe Gly Tyr
                60                  65

CCA CCA CTG ACA AAC GTC CTG GCA AGT TTC TTT GGC AAG CTG                700
Pro Pro Leu Thr Asn Val Leu Ala Ser Phe Phe Gly Lys Leu
70                  75                  80

CTG GGA CAG GAG ATG GAC CCA CTC ACG AAT GTG CTG GTG ACA                742
Leu Gly Gln Glu Met Asp Pro Leu Thr Asn Val Leu Val Thr
    85                  90                  95

GTG GGT GCC TAT GGG GCC TTG TTC ACA GCC TTT CAG GCC CTG                784
Val Gly Ala Tyr Gly Ala Leu Phe Thr Ala Phe Gln Ala Leu
        100                 105                 110

GTG GAT GAA GGA GAT GAG GTC ATC ATC ATG GAA CCT GCT TTT                826
Val Asp Glu Gly Asp Glu Val Ile Ile Met Glu Pro Ala Phe
            115                 120                 125

GAC TGT TAT GAA CCC ATG ACA ATG ATG GCT GGA GGT TGC CCT                868
Asp Cys Tyr Glu Pro Met Thr Met Met Ala Gly Gly Cys Pro
                130                 135

GTG TTC GTG ACT CTG AAG CCG AGC CCT GCT CCT AAG GGG AAA                910
Val Phe Val Thr Leu Lys Pro Ser Pro Ala Pro Lys Gly Lys
140                 145                 150

CTG GGA GCC AGC AAT GAT TGG CAA CTG GAT CCT GCA GAA CTG                952
Leu Gly Ala Ser Asn Asp Trp Gln Leu Asp Pro Ala Glu Leu
    155                 160                 165

GCC AGC AAG TTC ACA CCT CGC ACC AAG GTC CTG GTC CTC AAC                994
Ala Ser Lys Phe Thr Pro Arg Thr Lys Val Leu Val Leu Asn
        170                 175                 180

ACA CCC AAC AAC CCT TTA GGA AAG GTA TTC TCT AGG ATG GAG                1036
Thr Pro Asn Asn Pro Leu Gly Lys Val Phe Ser Arg Met Glu
            185                 190                 195

CTG GAG CTG GTG GCT AAT CTG TGC CAG CAG CAC GAT GTC GTG                1078
Leu Glu Leu Val Ala Asn Leu Cys Gln Gln His Asp Val Val
                200                 205

TGC ATC TCT GAT GAG GTC TAC CAG TGG CTG GTC TAT GAC GGG                1120
Cys Ile Ser Asp Glu Val Tyr Gln Trp Leu Val Tyr Asp Gly
210                 215                 220

CAC CAG CAC GTC AGC ATC GCC AGC CTC CCT GGC ATG TGG GAT                1162
His Gln His Val Ser Ile Ala Ser Leu Pro Gly Met Trp Asp
    225                 230                 235

CGG ACC CTG ACC ATC GGC AGT GCA GGC AAA AGC TTC AGT GCC                1204
Arg Thr Leu Thr Ile Gly Ser Ala Gly Lys Ser Phe Ser Ala
        240                 245                 250

ACT GGC TGG AAG GTG GGC TGG GTC ATG GGT CCA GAT AAC ATC                1246
Thr Gly Trp Lys Val Gly Trp Val Met Gly Pro Asp Asn Ile
            255                 260                 265

ATG AAG CAC CTG AGG ACA GTG CAC CAG AAT TCT ATC TTC CAC                1288
Met Lys His Leu Arg Thr Val His Gln Asn Ser Ile Phe His
                270                 275

TGC CCC ACC CAG GCC CAG GCT GCA GTA GCC CAG TGC TTT GAG                1330
Cys Pro Thr Gln Ala Gln Ala Ala Val Ala Gln Cys Phe Glu
280                 285                 290
```

```
CGG GAG CAG CAA CAC TTT GGA CAA CCC AGC AGC TAC TTT TTG                    1372
Arg Glu Gln Gln His Phe Gly Gln Pro Ser Ser Tyr Phe Leu
    295                 300                 305

CAG CTG CCA CAG GCC ATG GAG CTG AAC CGA GAC CAC ATG ATC                    1414
Gln Leu Pro Gln Ala Met Glu Leu Asn Arg Asp His Met Ile
        310                 315                 320

CGT AGC CTG CAG TCA GTG GGC CTC AAG CTC TGG ATC TCC CAG                    1456
Arg Ser Leu Gln Ser Val Gly Leu Lys Leu Trp Ile Ser Gln
            325                 330                 335

GGG AGC TAC TTC CTC ATT GCA GAC ATC TCA GAC TTC AAG AGC                    1498
Gly Ser Tyr Phe Leu Ile Ala Asp Ile Ser Asp Phe Lys Ser
                340                 345

AAG ATG CCT GAC CTG CCC GGA GCT GAG GAT GAG CCT TAT GAC                    1540
Lys Met Pro Asp Leu Pro Gly Ala Glu Asp Glu Pro Tyr Asp
350                 355                 360

AGA CGC TTT GCC AAG TGG ATG ATC AAA AAC ATG GGC TTG GTG                    1582
Arg Arg Phe Ala Lys Trp Met Ile Lys Asn Met Gly Leu Val
    365                 370                 375

GGC ATC CCT GTC TCC ACA TTC TTC AGT CGG CCC CAT CAG AAG                    1624
Gly Ile Pro Val Ser Thr Phe Phe Ser Arg Pro His Gln Lys
        380                 385                 390

GAC TTT GAC CAC TAC ATC CGA TTC TGT TTT GTC AAG GAC AAG                    1666
Asp Phe Asp His Tyr Ile Arg Phe Cys Phe Val Lys Asp Lys
            395                 400                 405

GCC ACA CTC CAG GCC ATG GAT GAG AGA CTG CGC AAG TGG AAA                    1708
Ala Thr Leu Gln Ala Met Asp Glu Arg Leu Arg Lys Trp Lys
                410                 415

GAG CTC CAA CCC TGAGGAGGCT GCCCTCAGCC CCACCTCGAA                           1750
Glu Leu Gln Pro
420

CACAGGCCTC AGCTATGCCT TAGCACAGGG ATGGCACTGG AGGGCCCAGC                     1800

TGTGTGACTG CGCATGTTTC CAGAAAAGAG GCCATGTCTT GGGGGTTGAA                     1850

GCCATCCTTT CCCAGTGTCC ATCTGGACTA TTGGGTTGGG GGCCAGTTCT                     1900

GGGTCTCAGC CTACTCCTCT GTAGGTTGCC TGTAGGGTTT TGATTGTTTC                     1950

TGGCCTCTCT GCCTGGGGCA GGAAAGGGTG GAATATCAGG CCCGGTACCA                     2000

CCTTAGCCCT GCCGAGGCTC TGTGGCTTCT CTACATCTTC TCCTGTGACC                     2050

TCAGGATGTT GCTACTGTTC CTAATAAAGT TTTAAGTTAT TAGGACCCTC                     2100

A                                                                         2101

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION:   /desc = "oligonucleotide primer"

(xi) SEQUENCE DESCRIPTION: SEQ ID NO: 6:

CAGGGCCTGG AAGGCTGTGA                                                        20

(2) INFORMATION FOR SEQ ID NO: 7:

(i) SEQUENCE CHARACTERISTICS:
        (A) LENGTH: 20 base pairs
        (B) TYPE: nucleic acid
```

(C) STRANDEDNESS: single
            (D) TOPOLOGY: linear (ii) MOLECULE TYPE: other nucleic acid
            (A) DESCRIPTION:    /desc = "oligonucleotide"

(xi) SEQUENCE DESCRIPTION: SEQ ID NO: 7:

ATAGCCACCA ACAGTCACCA                                                    20

(2) INFORMATION FOR SEQ ID NO: 8:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "oligonucleotide"

(xi) SEQUENCE DESCRIPTION: SEQ ID NO: 8:

GACTCGAGTC GACATCGATT TTTTTTTTTT TTTTT                                   35

(2) INFORMATION FOR SEQ ID NO: 9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "oligonucleotide"

(xi) SEQUENCE DESCRIPTION: SEQ ID NO: 9:

GACTCGAGTC GACATCGA                                                      18

(2) INFORMATION FOR SEQ ID NO: 10:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "oligonucleotide"

(xi) SEQUENCE DESCRIPTION: SEQ ID NO: 10:

ACCACTGACG AAGATCCTGG CAAGTTTCTT TGGGGAGC                                 38

(2) INFORMATION FOR SEQ ID NO: 11:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "oligonucleotide linker"

(xi) SEQUENCE DESCRIPTION: SEQ ID NO: 11:

TGTCCTCGAG ACCATGGCCA AACAGCTC                                           28

(2) INFORMATION FOR SEQ ID NO: 12:

(i) SEQUENCE CHARACTERISTICS:
            (A) LENGTH: 22 base pairs

```
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "oligonucleotide primer"

(xi) SEQUENCE DESCRIPTION: SEQ ID NO: 12:

GTAATACGAC TCACTATAGG GC                                                  22

(2) INFORMATION FOR SEQ ID NO: 13:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "oligonucleotide primer"

(xi) SEQUENCE DESCRIPTION: SEQ ID NO: 13:

TGTCCTCGAG CGCTCTAGAA CTAGTGGATC                                          30

(2) INFORMATION FOR SEQ ID NO:14:

(i) SEQUENCE CHARACTERISTICS:
            (A) LENGTH:  23 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:  SEQ ID NO:14:

Leu Gln Ala Xaa Xaa Leu Asp Gly Ile Asp Gln Asn
1               5                  10

Leu Xaa Val Glu Phe Gly Lys Thr Xaa Glu Tyr
            15                  20

(2) INFORMATION FOR SEQ ID NO:15:

(i) SEQUENCE CHARACTERISTICS:
            (A) LENGTH:  16 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:  SEQ ID NO:15:

Xaa Xaa Leu Pro Gly Ala Glu Asp Gly Pro Tyr
1               5                  10

Asp Arg Arg Xaa Ala
            15

(2) INFORMATION FOR SEQ ID NO:16:

(i) SEQUENCE CHARACTERISTICS:
            (A) LENGTH:  14 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:  SEQ ID NO:16:

Arg Leu Asp Gly Ile Asp Gln Asn Leu
1               5
```

```
Ser Val Glu Phe Gly
 10

(2) INFORMATION FOR SEQ ID NO:17:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Xaa Glu Leu Glu Leu Val Ala Asn Leu Cys Gln Gln
 1               5                  10

His Asp Val Cys Ile Ser Asp Glu Val Tyr Gln Gln
         15                  20

Val Tyr Asp Leu Gly His Gln
 25              30

(2) INFORMATION FOR SEQ ID NO:18:

(i) SEQUENCE CHARACTERISTICS:
        (A) LENGTH: 1893 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:
```

| | |
|---|---|
| AAACTGACCA AGGAGTATGA TCAATCCCGT CCAGCCTCCG AGCCTGCAGC | 50 |
| CGTTTGGTCA TGGTGAGCTG CTTCAGCTAA CAATTGCACT GACAGTGCTC | 100 |
| TTGAGCCAAG TTGCTTCTGG GCGGAAGTAG TCCATCTAGG GCTCGGCCTC | 150 |
| TTTAAAGAAA CAGACTTCTG CAACCTTGGG ACTACGTTTG GGGTCGCCGG | 200 |
| CTATTGGACG GAGCAGCGCA ATTGTTAGCT GAAGCAGCTC ACC ATG ACC<br>                                                       Met Thr<br>                                                        1 | 249 |
| AAA CGG CTG CAG GCT CGG AGG CTG GAC GGG ATT GAT CAA AAC<br>Lys Arg Leu Gln Ala Arg Arg Leu Asp Gly Ile Asp Gln Asn<br> 5                  10                  15 | 291 |
| CTC TGG GTG GAG TTT GGC AAA CTG ACC AAG GAG TAT GAC GTC<br>Leu Trp Val Glu Phe Gly Lys Leu Thr Lys Glu Tyr Asp Val<br> 20              25                  30 | 333 |
| GTG AAC TTG GGT CAG GGC TTC CCT GAC TTC TCG CCT CCG GAC<br>Val Asn Leu Gly Gln Gly Phe Pro Asp Phe Ser Pro Pro Asp<br> 35                 40 | 375 |
| TTT GCA ACG CAA GCT TTT CAG CAG GCT ACC AGT GGG AAC TTC<br>Phe Ala Thr Gln Ala Phe Gln Gln Ala Thr Ser Gly Asn Phe<br> 45                 50                  55 | 417 |
| ATG CTC AAC CAG TAC ACC AGG GCA TTT GGT TAC CCA CCA CTG<br>Met Leu Asn Gln Tyr Thr Arg Ala Phe Gly Tyr Pro Pro Leu<br> 60              65                  70 | 459 |
| ACA AAC GTC CTG GCA AGT TTC TTT GGC AAG CTG CTG GGA CAG<br>Thr Asn Val Leu Ala Ser Phe Phe Gly Lys Leu Leu Gly Gln<br> 75              80                  85 | 501 |
| GAG ATG GAC CCA CTC ACG AAT GTG CTG GTG ACA GTG GGT GCC<br>Glu Met Asp Pro Leu Thr Asn Val Leu Val Thr Val Gly Ala<br> 90              95                  100 | 543 |
| TAT GGG GCC TTG TTC ACA GCC TTT CAG GCC CTG GTG GAT GAA<br>Tyr Gly Ala Leu Phe Thr Ala Phe Gln Ala Leu Val Asp Glu<br> 105                110 | 585 |

```
GGA GAT GAG GTC ATC ATC ATG GAA CCT GCT TTT GAC TGT TAT                   627
Gly Asp Glu Val Ile Ile Met Glu Pro Ala Phe Asp Cys Tyr
115             120                 125

GAA CCC ATG ACA ATG ATG GCT GGA GGT TGC CCT GTG TTC GTG                   669
Glu Pro Met Thr Met Met Ala Gly Gly Cys Pro Val Phe Val
130             135                 140

ACT CTG AAG CCG AGC CCT GCT CCT AAG GGG AAA CTG GGA GCC                   711
Thr Leu Lys Pro Ser Pro Ala Pro Lys Gly Lys Leu Gly Ala
145             150                 155

AGC AAT GAT TGG CAA CTG GAT CCT GCA GAA CTG GCC AGC AAG                   753
Ser Asn Asp Trp Gln Leu Asp Pro Ala Glu Leu Ala Ser Lys
160             165                 170

TTC ACA CCT CGC ACC AAG GTC CTG GTC CTC AAC ACA CCC AAC                   795
Phe Thr Pro Arg Thr Lys Val Leu Val Leu Asn Thr Pro Asn
175             180

AAC CCT TTA GGA AAG GTA TTC TCT AGG ATG GAG CTG GAG CTG                   837
Asn Pro Leu Gly Lys Val Phe Ser Arg Met Glu Leu Glu Leu
185             190                 195

GTG GCT AAT CTG TGC CAG CAG CAC GAT GTC GTG TGC ATC TCT                   879
Val Ala Asn Leu Cys Gln Gln His Asp Val Val Cys Ile Ser
200             205                 210

GAT GAG GTC TAC CAG TGG CTG GTC TAT GAC GGG CAC CAG CAC                   921
Asp Glu Val Tyr Gln Trp Leu Val Tyr Asp Gly His Gln His
215             220                 225

GTC AGC ATC GCC AGC CTC CCT GGC ATG TGG GAT CGG ACC CTG                   963
Val Ser Ile Ala Ser Leu Pro Gly Met Trp Asp Arg Thr Leu
230             235                 240

ACC ATC GGC AGT GCA GGC AAA AGC TTC AGT GCC ACT GGC TGG                  1005
Thr Ile Gly Ser Ala Gly Lys Ser Phe Ser Ala Thr Gly Trp
245             250

AAG GTG GGC TGG GTC ATG GGT CCA GAT AAC ATC ATG AAG CAC                  1047
Lys Val Gly Trp Val Met Gly Pro Asp Asn Ile Met Lys His
255             260                 265

CTG AGG ACA GTG CAC CAG AAT TCT ATC TTC CAC TGC CCC ACC                  1089
Leu Arg Thr Val His Gln Asn Ser Ile Phe His Cys Pro Thr
270             275                 280

CAG GCC CAG GCT GCA GTA GCC CAG TGC TTT GAG CGG GAG CAG                  1131
Gln Ala Gln Ala Ala Val Ala Gln Cys Phe Glu Arg Glu Gln
285             290                 295

CAA CAC TTT GGA CAA CCC AGC AGC TAC TTT TTG CAG CTG CCA                  1173
Gln His Phe Gly Gln Pro Ser Ser Tyr Phe Leu Gln Leu Pro
300             305                 310

CAG GCC ATG GAG CTG AAC CGA GAC CAC ATG ATC CGT AGC CTG                  1215
Gln Ala Met Glu Leu Asn Arg Asp His Met Ile Arg Ser Leu
315             320

CAG TCA GTG GGC CTC AAG CTC TGG ATC TCC CAG GGG AGC TAC                  1257
Gln Ser Val Gly Leu Lys Leu Trp Ile Ser Gln Gly Ser Tyr
325             330                 335

TTC CTC ATT GCA GAC ATC TCA GAC TTC AAG AGC AAG ATG CCT                  1299
Phe Leu Ile Ala Asp Ile Ser Asp Phe Lys Ser Lys Met Pro
340             345                 350

GAC CTG CCC GGA GCT GAG GAT GAG CCT TAT GAC AGA CGC TTT                  1341
Asp Leu Pro Gly Ala Glu Asp Glu Pro Tyr Asp Arg Arg Phe
355             360                 365

GCC AAG TGG ATG ATC AAA AAC ATG GGC TTG GTG GGC ATC CCT                  1383
Ala Lys Trp Met Ile Lys Asn Met Gly Leu Val Gly Ile Pro
370             375                 380

GTC TCC ACA TTC TTC AGT CGG CCC CAT CAG AAG GAC TTT GAC                  1425
Val Ser Thr Phe Phe Ser Arg Pro His Gln Lys Asp Phe Asp
```

```
385                 390
CAC TAC ATC CGA TTC TGT TTT GTC AAG GAC AAG GCC ACA CTC          1467
His Tyr Ile Arg Phe Cys Phe Val Lys Asp Lys Ala Thr Leu
395                 400                 405

CAG GCC ATG GAT GAG AGA CTG CGC AAG TGG AAA GAG CTC CAA          1509
Gln Ala Met Asp Glu Arg Leu Arg Lys Trp Lys Glu Leu Gln
410                 415                 420

CCC TGAGGAGGCT GCCCTCAGCC CCACCTCGAA CACAGGCCTC AGCTATGCCT       1562
Pro

TAGCACAGGG ATGGCACTGG AGGGCCCAGC TGTGTGACTG CGCATGTTTC           1612

CAGAAAAGAG GCCATGTCTT GGGGGTTGAA GCCATCCTTT CCCAGTGTCC           1662

ATCTGGACTA TTGGGTTGGG GGCCAGTTCT GGGTCTCAGC CTACTCCTCT           1712

GTAGGTTGCC TGTAGGGTTT TGATTGTTTC TGGCCTCTCT GCCTGGGGCA           1762

GGAAAGGGTG GAATATCAGG CCCGGTACCA CCTTAGCCCT GCCGAGGCTC           1812

TGTGGCTTCT CTACATCTTC TCCTGTGACC TCAGGATGTT GCTACTGTTC           1862

CTAATAAAGT TTTAAGTTAT TAGGACCCTC A                               1893

(2) INFORMATION FOR SEQ ID NO:19:

(i) SEQUENCE CHARACTERISTICS:
        (A) LENGTH: 2304 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

GGGCGACTCT AGATTTTTTT TTTTTTTTAC CTTCTACCTT TTATTGTCAC             50

GTGAACCATG GTCCTACAGG CTGCTGACAA GCTTGGCTGA GCAGGGATCC            100

CAGGGGCGTC GGCAGGAGAT GAGGAAGGGT TGCTGGGAGG GCTTGGCCTC            150

TTCCTTGAGA AGACAGCAAA TGTATCCAGC CTAGATTAAG GGTAGGGCAT            200

CCCCTATCCC TGTCAGTGGG CCTAGATCTC AGAGCCCCAC ATTAAAGACT            250

GCTAATGGGT CAGAAATGGG GGTCCCTTAG ATGGGGGTAG GCAGCAAGGC            300

CCTCCCTCCA GTGTTCTCAT TCTGTTCCGG TTTCATTTGT TGTGTCCAGG            350

GACGGTGAAG CAGATACCAG TCTCAAGCCC CAGGGTGCAG GAAGACGGGA            400

AATGGGAAAA TGGAAACATT CTTCAAGTGA CCAGAGCACT CTGCCGGGGA            450

CAAAAGACTT TGCCTTGAAC GCGTAGTGGA GAAGCTACAA ACCCCAGGTC            500

CCAGTGGCCT GATTGACTTA GGGTCTCAGC TGGCCCAAAA CTCAGTGTGT            550

AGATCAGACT GATCTCAAAC TCACAGAGAT CTCCCTGCCT TTGCCTGCTG            600

AGTCCTGGGA TTAAAGGC ATG AAT CAC AGT ACC TGG TGC CTT TTC           645
                   Met Asn His Ser Thr Trp Cys Leu Phe
                   1               5

TTT AAA AAG CTC ACC ATG ACC AAA CGG CTG CAG GCT CGG AGG           687
Phe Lys Lys Leu Thr Met Thr Lys Arg Leu Gln Ala Arg Arg
10                  15                  20

CTG GAC GGG ATT GAT CAA AAC CTC TGG GTG GAG TTT GGC AAA           729
Leu Asp Gly Ile Asp Gln Asn Leu Trp Val Glu Phe Gly Lys
25                  30                  35

CTG ACC AAG GAG TAT GAC GTC GTG AAC TTG GGT CAG GGC TTC           771
Leu Thr Lys Glu Tyr Asp Val Val Asn Leu Gly Gln Gly Phe
40                  45                  50
```

```
CCT GAC TTC TCG CCT CCG GAC TTT GCA ACG CAA GCT TTT CAG                    813
Pro Asp Phe Ser Pro Pro Asp Phe Ala Thr Gln Ala Phe Gln
55              60                  65

CAG GCT ACC AGT GGG AAC TTC ATG CTC AAC CAG TAC ACC AGG                    855
Gln Ala Thr Ser Gly Asn Phe Met Leu Asn Gln Tyr Thr Arg
70              75

GCA TTT GGT TAC CCA CCA CTG ACA AAC GTC CTG GCA AGT TTC                    897
Ala Phe Gly Tyr Pro Pro Leu Thr Asn Val Leu Ala Ser Phe
80              85                  90

TTT GGC AAG CTG CTG GGA CAG GAG ATG GAC CCA CTC ACG AAT                    939
Phe Gly Lys Leu Leu Gly Gln Glu Met Asp Pro Leu Thr Asn
95              100                 105

GTG CTG GTG ACA GTG GGT GCC TAT GGG GCC TTG TTC ACA GCC                    981
Val Leu Val Thr Val Gly Ala Tyr Gly Ala Leu Phe Thr Ala
110             115                 120

TTT CAG GCC CTG GTG GAT GAA GGA GAT GAG GTC ATC ATC ATG                   1023
Phe Gln Ala Leu Val Asp Glu Gly Asp Glu Val Ile Ile Met
125             130                 135

GAA CCT GCT TTT GAC TGT TAT GAA CCC ATG ACA ATG ATG GCT                   1065
Glu Pro Ala Phe Asp Cys Tyr Glu Pro Met Thr Met Met Ala
140             145

GGA GGT TGC CCT GTG TTC GTG ACT CTG AAG CCG AGC CCT GCT                   1107
Gly Gly Cys Pro Val Phe Val Thr Leu Lys Pro Ser Pro Ala
150             155                 160

CCT AAG GGG AAA CTG GGA GCC AGC AAT GAT TGG CAA CTG GAT                   1149
Pro Lys Gly Lys Leu Gly Ala Ser Asn Asp Trp Gln Leu Asp
165             170                 175

CCT GCA GAA CTG GCC AGC AAG TTC ACA CCT CGC ACC AAG GTC                   1191
Pro Ala Glu Leu Ala Ser Lys Phe Thr Pro Arg Thr Lys Val
180             185                 190

CTG GTC CTC AAC ACA CCC AAC AAC CCT TTA GGA AAG GTA TTC                   1233
Leu Val Leu Asn Thr Pro Asn Asn Pro Leu Gly Lys Val Phe
195             200                 205

TCT AGG ATG GAG CTG GAG CTG GTG GCT AAT CTG TGC CAG CAG                   1275
Ser Arg Met Glu Leu Glu Leu Val Ala Asn Leu Cys Gln Gln
210             215

CAC GAT GTC GTG TGC ATC TCT GAT GAG GTC TAC CAG TGG CTG                   1317
His Asp Val Val Cys Ile Ser Asp Glu Val Tyr Gln Trp Leu
220             225                 230

GTC TAT GAC GGG CAC CAG CAC GTC AGC ATC GCC AGC CTC CCT                   1359
Val Try Asp Gly His Gln His Val Ser Ile Ala Ser Leu Pro
235             240                 245

GGC ATG TGG GAT CGG ACC CTG ACC ATC GGC AGT GCA GGC AAA                   1401
Gly Met Trp Asp Arg Thr Leu Thr Ile Gly Ser Ala Gly Lys
250             255                 260

AGC TTC AGT GCC ACT GGC TGG AAG GTG GGC TGG GTC ATG GGT                   1443
Ser Phe Ser Ala Thr Gly Trp Lys Val Gly Trp Val Met Gly
265             270                 275

CCA GAT AAC ATC ATG AAG CAC CTG AGG ACA GTG CAC CAG AAT                   1485
Pro Asp Asn Ile Met Lys His Leu Arg Thr Val His Gln Asn
280             285

TCT ATC TTC CAC TGC CCC ACC CAG GCC CAG GCT GCA GTA GCC                   1527
Ser Ile Phe His Cys Pro Thr Gln Ala Gln Ala Ala Val Ala
290             295                 300

CAG TGC TTT GAG CGG GAG CAG CAA CAC TTT GGA CAA CCC AGC                   1569
Gln Cys Phe Glu Arg Glu Gln Gln His Phe Gly Gln Pro Ser
305             310                 315

AGC TAC TTT TTG CAG CTG CCA CAG GCC ATG GAG CTG AAC CGA                   1611
Ser Tyr Phe Leu Gln Leu Pro Gln Ala Met Glu Leu Asn Arg
```

```
               320                 325                 330
GAC CAC ATG ATC CGT AGC CTG CAG TCA GTG GGC CTC AAG CTC         1653
Asp His Met Ile Arg Ser Leu Gln Ser Val Gly Leu Lys Leu
335                 340                 345

TGG ATC TCC CAG GGG AGC TAC TTC CTC ATT GCA GAC ATC TCA         1695
Trp Ile Ser Gln Gly Ser Tyr Phe Leu Ile Ala Asp Ile Ser
350                 355

GAC TTC AAG AGC AAG ATG CCT GAC CTG CCC GGA GCT GAG GAT         1737
Asp Phe Lys Ser Lys Met Pro Asp Leu Pro Gly Ala Glu Asp
360                 365                 370

GAG CCT TAT GAC AGA CGC TTT GCC AAG TGG ATG ATC AAA AAC         1779
Glu Pro Tyr Asp Arg Arg Phe Ala Lys Trp Met Ile Lys Asn
375                 380                 385

ATG GGC TTG GTG GGC ATC CCT GTC TCC ACA TTC TTC AGT CGG         1821
Met Gly Leu Val Gly Ile Pro Val Ser Thr Phe Phe Ser Arg
390                 395                 400

CCC CAT CAG AAG GAC TTT GAC CAC TAC ATC CGA TTC TGT TTT         1863
Pro His Gln Lys Asp Phe Asp His Tyr Ile Arg Phe Cys Phe
405                 410                 415

GTC AAG GAC AAG GCC ACA CTC CAG GCC ATG GAT GAG AGA CTG         1905
Val Lys Asp Lys Ala Thr Leu Gln Ala Met Asp Glu Arg Leu
420                 425

CGC AAG TGG AAA GAG CTC CAA CCC TGAGGAGGCT GCCCTCAGCC           1949
Arg Lys Trp Lys Glu Leu Gln Pro
430                 435

CCACCTCGAA CACAGGCCTC AGCTATGCCT TAGCACAGGG ATGGCACTGG          1999

AGGGCCCAGC TGTGTGACTG CGCATGTTTC CAGAAAAGAG GCCATGTCTT          2049

GGGGGTTGAA GCCATCCTTT CCCAGTGTCC ATCTGGACTA TTGGGTTGGG          2099

GGCCAGTTCT GGGTCTCAGC CTACTCCTCT GTAGGTTGCC TGTAGGGTTT          2149

TGATTGTTTC TGGCCTCTCT GCCTGGGGCA GGAAAGGGTG GAATATCAGG          2199

CCCGGTACCA CCTTAGCCCT GCCGAGGCTC TGTGGCTTCT CTACATCTTC          2249

TCCTGTGACC TCAGGATGTT GCTACTGTTC CTAATAAAGT TTTAAGTTAT          2299

TAGGA                                                           2304

(2) INFORMATION FOR SEQ ID NO:20:

(i) SEQUENCE CHARACTERISTICS:
        (A) LENGTH:  26 base pairs
        (B) TYPE:  nucleic acid
        (C) STRANDEDNESS:  single
        (D) TOPOLOGY:  linear (ii) MOLECULE TYPE:  DNA (synthetic)

(xi) SEQUENCE DESCRIPTION:  SEQ ID NO:20:

AAYYTNTGYC ARCARCAYGA YGTNGT                                    26

(2) INFORMATION FOR SEQ ID NO:21:

(i) SEQUENCE CHARACTERISTICS:
        (A) LENGTH:  26 base pairs
        (B) TYPE:  nucleic acid
        (C) STRANDEDNESS:  single
        (D) TOPOLOGY:  linear (ii) MOLECULE TYPE:  DNA (synthetic)

(xi) SEQUENCE DESCRIPTION:  SEQ ID NO:21:

ACNACRTCRT GYTGYTGRCA NARRTT                                    26
```

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:22:

ACNGANARRT TYTGRTCDAT NCCRTC                                      26

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:23:

GAYGGNATHG AYCARAAYYT NTCNGT                                      26

(2) INFORMATION FOR SEQ ID NO:24:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:24:

GCTAGTCGAC ACNACRTCRT GYTGYTGRCA NARRTT                          36

(2) INFORMATION FOR SEQ ID NO:25:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:25:

GATCGTCGAC GAYGGNATHG AYCARAAYYT NTCNGT                          36

(2) INFORMATION FOR SEQ ID NO:26:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:26:

TGTCCTCGAG ACCATGACCA AACGGCTGCA GGCTCGGA                        38

(2) INFORMATION FOR SEQ ID NO:27:

```
(i) SEQUENCE CHARACTERISTICS:
    (A) LENGTH:  35 base pairs
    (B) TYPE:  nucleic acid
    (C) STRANDEDNESS:  single
    (D) TOPOLOGY:  linear (ii) MOLECULE TYPE:  DNA (xi) SEQUENCE DESCRIPTION:  SEQ ID NO:27:

GTACCTCGAG TCAGGGTTGG AGCTCTTTCC ACTTG                    35
```

We claim:

1. An isolated DNA sequence which encodes rat KAT enzyme, which comprises the sequence of the clone cDNA-1 (SEQ ID NO:18).

2. An isolated DNA sequence which encodes rat KAT enzyme, which comprises the sequence of the clone cDNA-2 (SEQ ID NO:19).

3. An isolated DNA sequence which encodes rat KAT enzyme, which comprises the sequence of the clone cDNA-3 (SEQ ID NO:5).

4. A vector comprising a cloned DNA sequence as defined in any one of claims 1 to 3.

5. A vector comprising a cloned DNA sequence as defined in any one of claims 1 to 3, wherein the vector is a plasmid.

6. A vector comprising a cloned DNA sequence as defined in any one of claims 1 to 3, wherein the vector is a virus.

7. A vector comprising a cloned DNA sequence as defined in any one of claims 3 to 5, wherein the vector is a retrovirus.

8. A host cell transformed with a vector comprising a cloned DNA sequence as defined in any one of claims 3 to 5.

9. A host cell transformed with a vector comprising a cloned DNA sequence as defined in any one of claims 3 to 5, wherein the cell is a mammalian cell.

10. A method of producing neuroactive kynurenic analogs comprising transforming cells useful for producing neuroactive kynurenic analogs with a vector comprising a cloned DNA sequence as defined in any one of claims 1 to 3, growing transformed cells in media supplemented with a kynurenine analog, collecting the produce kynurenic analog produced by the said transformed cells, and testing said kynurenic analogs for neuroactive properties.

11. A method of producing neuroactive kynurenic analogs comprising growing the host cell according to any one of claim 8 in media supplemented with a kynurenine analog, collecting said kynurenic analogs produced thereby, and testing said kynurenic analogs for neuroactive properties.

12. A method of producing neuroactive kynurenic analogs comprising growing the host cell according to claim 9 in media supplemented with a kynurenine analog, collecting said kynurenic analogs produced thereby, and testing said kynurenic analogs for neuroactive properties.

* * * * *